United States Patent
Ekoue-Kovi et al.

(10) Patent No.: US 10,457,817 B2
(45) Date of Patent: Oct. 29, 2019

(54) 2-MERCAPTOBENZIMIDAZOLE DERIVATIVES AS CORROSION INHIBITORS

(71) Applicant: Ecolab USA Inc., St. Paul, MN (US)

(72) Inventors: Kekeli Ekoue-Kovi, Rosenberg, TX (US); Neetu Tomar, Haryana (IN); Deepak Jadhav, Hindalaga (IN); Kim B. Peyton, Richmond, TX (US); Jennifer L. Sorrells, Houston, TX (US); Ian Michael Jones, Pittsburgh, PA (US)

(73) Assignee: Ecolab USA Inc., St. Paul, MN (US)

( * ) Notice: Subject to any disclaimer, the term of this patent is extended or adjusted under 35 U.S.C. 154(b) by 100 days.

(21) Appl. No.: 15/584,489

(22) Filed: May 2, 2017

(65) Prior Publication Data

US 2017/0313891 A1    Nov. 2, 2017

Related U.S. Application Data

(60) Provisional application No. 62/330,648, filed on May 2, 2016.

(51) Int. Cl.

| | |
|---|---|
| *C09D 5/08* | (2006.01) |
| *C10L 1/24* | (2006.01) |
| *C09D 7/63* | (2018.01) |
| *C07D 235/28* | (2006.01) |
| *C23F 11/16* | (2006.01) |
| *C23F 11/10* | (2006.01) |
| *C10L 10/04* | (2006.01) |

(52) U.S. Cl.
CPC .......... *C09D 5/086* (2013.01); *C07D 235/28* (2013.01); *C09D 7/63* (2018.01); *C10L 1/2443* (2013.01); *C10L 10/04* (2013.01); *C23F 11/10* (2013.01); *C23F 11/16* (2013.01); *C23F 11/165* (2013.01); *C10L 1/2456* (2013.01); *C10L 2200/0423* (2013.01); *C10L 2200/0446* (2013.01); *C10L 2270/023* (2013.01); *C10L 2270/026* (2013.01)

(58) Field of Classification Search
CPC ......... C09D 5/086; C09D 7/63; C10L 1/2443; C10L 10/04; C10L 2270/023; C10L 2200/0446; C10L 1/2456; C10L 2200/0423; C10L 2270/026; C23F 11/10; C23F 11/16; C23F 11/165; C07D 235/28
See application file for complete search history.

(56) References Cited

U.S. PATENT DOCUMENTS

| | | | |
|---|---|---|---|
| 3,663,561 A | 5/1972 | Blaha | |
| 4,351,945 A | 9/1982 | Brois et al. | |
| 5,102,568 A | 4/1992 | King et al. | |
| 5,552,069 A | 9/1996 | Avery et al. | |
| 7,776,800 B2 | 8/2010 | Lam et al. | |
| 2008/0171677 A1 | 7/2008 | Buck et al. | |
| 2009/0076279 A1* | 3/2009 | Rowland | ............... C07D 235/28 548/169 |
| 2015/0051125 A1 | 2/2015 | Ayame et al. | |
| 2015/0072907 A1 | 3/2015 | Iwasaki et al. | |
| 2015/0119305 A1 | 4/2015 | Nagakari et al. | |
| 2015/0203779 A1 | 7/2015 | Hanyuda et al. | |
| 2015/0203780 A1 | 7/2015 | Yagishita | |
| 2015/0210954 A1 | 7/2015 | Miyamoto | |

FOREIGN PATENT DOCUMENTS

| | | |
|---|---|---|
| CN | 104817781 A | 8/2015 |
| CN | 105239063 A | 1/2016 |
| EP | 0218816 B1 | 9/1990 |
| EP | 1 914 292 A1 | 4/2008 |
| GB | 910910 | 11/1962 |
| GB | 1103399 | 2/1968 |
| JP | 2004155881 A | 6/2004 |
| JP | 2007 186491 | 7/2007 |

OTHER PUBLICATIONS

Alvarez-Bustamante, R. et al., Electrochemical study of 2-mercaptoimidazole as a novel corrosion inhibitor for steels, Electrochimica Acta, vol. 54, Issue 23, Sep. 30, 2009, (Abstract only).

Liu, Lin et al., Corrosion inhibition and olecular structure of thiadiazole derivatives in sulfur-ethanol system, CIESC Journal, vol. 65, No. 10, Oct. 2014, (Abstract only).

Liu, Lin, Anti-corrosion behavior of thiadiazole derivatives for silver strip in hydrogen sulfide solutions, Anti-Corrosion Methods and Materials (2015), pp. 353-362.

Prakash, D. et al., Corrosion inhibition of mild steel in 20% HCl by some organic compounds, Indian Journal of Chemical Technology, vol. 13, Nov. 2006, pp. 555-560.

Zhang, Tianyi et al., Study on the electrochemical reduction of benzimidazole-2-thione and its 1-lauroyl derivative in organic solvent, Journal of Electroanalytical Chemistry 393 (1995) 55-59.

International Search Report and Written Opinion relating to PCT Patent Application No. PCT/US2017/030543 dated Jul. 31, 2017, 15 pages.

* cited by examiner

*Primary Examiner* — Peter F Godenschwager
*Assistant Examiner* — Andrew J. Oyer
(74) *Attorney, Agent, or Firm* — Stinson LLP

(57) ABSTRACT

The present invention generally relates to methods and compounds for preventing metal corrosion. More specifically, the method comprises contacting a hydrocarbon-containing liquid with a composition in an effective amount to prevent metal corrosion.

19 Claims, No Drawings

2-MERCAPTOBENZIMIDAZOLE DERIVATIVES AS CORROSION INHIBITORS

CROSS-REFERENCE TO RELATED APPLICATION

This application claims priority to U.S. Provisional Patent Application Ser. No. 62/330,648 filed on May 2, 2016, the disclosure of which is incorporated herein by reference in its entirety.

FIELD OF THE INVENTION

The present invention generally relates to methods for preventing metal corrosion. The methods comprise contacting a hydrocarbon-containing liquid with a composition in an amount effective to prevent metal corrosion.

BACKGROUND OF THE INVENTION

The use of oxygenates, i.e., a compound containing oxygen, as gasoline additives to reduce carbon monoxide and soot can increase air pollution, in particular ground-level ozone and smog. In addition, the use of ethanol alone or in gasoline blends can create problems for fuel equipment not designed to handle the more non-polar hydrocarbonaceous petroleum fractions commonly known as gasolines. The polarity and corrosivity of ethanol or ethanol-containing fuels can create new problems for the fuel industry.

These ethanol or ethanol-containing fuels can create engine wear from reduced naturally occurring lubricating species in the fuel and increased corrosion or increased deposit formation. Corrosion and deposit formation can reduce drivability or fuel economy, or even cause complete failure. Corrosion inhibitors are frequently deployed to mitigate these negative effects. Further, the use of fuel oxygenates has increased the need for effective corrosion inhibitors.

In general, corrosion inhibitors protect a metal surface through the formation of a passivation film on the metal surface. This passivation layer oil wets the metal surface, which in turn prevents contact of the metal from the corrosive nature of the fluids. Typically, corrosion inhibitor formulations of this type contain a variety of aliphatic organic surfactant molecules ranging from, but not limited to, amines, quaternary amines, imidazolines, phosphate esters, amides, carboxylic acids, or combinations thereof.

Often, organic thiol compounds are added in low concentrations to these corrosion inhibitor components to increase the effectiveness of the traditional corrosion inhibitor molecules. It is believed that these organic thiol molecules create a stronger passivation layer on the metal surface which also increases the persistence of the protective film. In most examples, the sulfur based component consists of a primary thio/mercaptan (e.g., 2-mercaptoethanol or mercaptoacetic acid). In some instances, however, such thiol based formulations can degrade at elevated temperatures (e.g., during storage at elevated temperatures) to release volatile sulfur-containing vapor/gases (e.g., mercaptans, sulfur dioxide, hydrogen sulfide, and/or carbonyl sulfide).

Recently, government guidelines were released requiring gasoline being sold within the United States to contain less than 10 ppm sulfur on an average annual basis starting on Jan. 1, 2017. As a result, additives, e.g., corrosion inhibitors, must also have a low sulfur content or have a waiver from the EPA to allow them to be added, if the addition of the additive causes the finished gasoline to exceed the 10 ppm sulfur annual average.

Thus, there is a need to develop effective corrosion inhibitors that contain a low sulfur content.

SUMMARY OF THE INVENTION

One aspect of the invention is directed to a method for preventing metal corrosion. The method comprising contacting an effective amount of an anticorrosion composition with a hydrocarbon-containing liquid, the hydrocarbon-containing liquid being in contact with a metal. The anticorrosion composition comprising a solvent and a compound of Formula I or II:

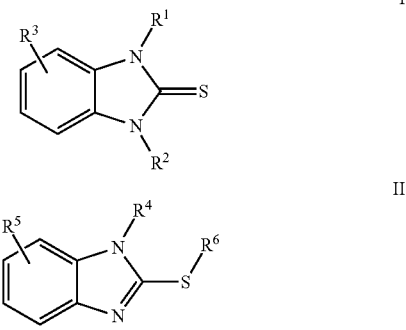

wherein $R^1$ and $R^2$ are independently substituted alkyl or unsubstituted alkyl; $R^3$ is hydrogen, substituted alkyl, or unsubstituted alkyl; $R^4$ is hydrogen, substituted alkyl, unsubstituted alkyl, substituted aryl, or unsubstituted aryl; $R^5$ is hydrogen, substituted alkyl, or unsubstituted alkyl; $R^6$ is hydrogen, substituted alkyl, unsubstituted alkyl, —S-heterocyclo, or —S-alkyl.

Another aspect of the invention is directed to a method for preventing metal corrosion. The method comprising contacting an effective amount of an anticorrosion composition with a hydrocarbon-containing liquid, the hydrocarbon-containing liquid being in contact with a metal. The anticorrosion composition comprising a solvent, a compound of Formula I or II, and further comprising a compound of Formula III or IV:

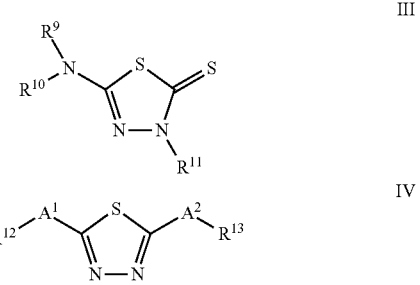

wherein $R^9$ and $R^{10}$ are independently hydrogen, substituted alkyl, unsubstituted alkyl, or together form an alkyliminyl; $R^{11}$ is independently substituted alkyl, unsubstituted alkyl, substituted alkenyl, or unsubstituted alkenyl; $R^{12}$ and $R^{13}$ are independently hydrogen, substituted alkyl, unsubstituted alkyl, substituted alkenyl, or unsubstituted alkenyl; $A^1$ and $A^2$ are independently —S—, —N=C—, or —NR$^{14}$; R$^{14}$ is hydrogen or substituted alkyl, or unsubstituted alkyl.

A further aspect of the invention is directed to a compound of Formula IA

IA wherein R$^1$ and R$^2$ are independently hydrogen or C$_6$ to C$_{30}$ substituted alkyl, where at least one of R$^1$ and R$^2$ are C$_6$ to C$_{30}$ substituted alkyl; and R$^3$ is hydrogen, substituted alkyl, or unsubstituted alkyl.

Other objects and features will be in part apparent and in part pointed out hereinafter.

DESCRIPTION OF THE PREFERRED EMBODIMENTS

Anticorrosion compositions that are effective at preventing silver and copper corrosion are provided. In particular, these anticorrosion compositions are well suited for inhibiting corrosion in a hydrocarbon-containing liquid, such as gasoline, diesel, naphtha, jet fuel, kerosene, or a combination thereof. One of the challenges of inhibiting corrosion of a metal surface (e.g., particularly silver and copper) in contact with gasoline and related hydrocarbons is the regulation requiring low sulfur anticorrosion compositions. Thus, the anticorrosion compositions described herein are effective to reduce corrosion of silver and copper in oil refining processes and also have a lower concentration of sulfur as compared to commercially available agents.

The sulfur content of the anticorrosion agent of Formula I or II described herein is from about 4 mass % to about 25 mass % calculated by dividing the molecular weight of the sulfur in the agent by the total molecular weight of the agent and multiplying by 100.

The present invention is directed towards a method for preventing metal corrosion. The method comprising contacting an effective amount of an anticorrosion composition with a hydrocarbon-containing liquid, the hydrocarbon-containing liquid being in contact with a metal. The anticorrosion composition comprising a solvent and a compound of Formula I or II:

I

II wherein R$^1$ and R$^2$ are independently substituted alkyl or unsubstituted alkyl; R$^3$ is hydrogen, substituted alkyl, or unsubstituted alkyl; R$^4$ is hydrogen, substituted alkyl, unsubstituted alkyl, substituted aryl, or unsubstituted aryl; R$^5$ is hydrogen, substituted alkyl, or unsubstituted alkyl; R$^6$ is hydrogen, substituted alkyl, unsubstituted alkyl, —S-heterocyclo, or —S-alkyl.

The compound of Formula I or II can have at least one of R$^4$ or R$^5$ is other than hydrogen.

The compound of Formula I or II can have R$^1$, R$^2$, and R$^4$ independently be substituted alkyl wherein one or more of the —CH$_2$— groups is replaced with a —C(O)—, or —O—, or one or more of the carbon atoms of the alkyl group is substituted with an amine group.

The compound of Formula I or II can have R$^1$, R$^2$, and R$^4$ independently be —(CHR$^{22}$)$_n$—NR$^{20}$R$^{21}$, wherein n is an integer from 1 to 4, R$^{20}$ and R$^{21}$ are independently alkyl, and R$^{22}$ is hydrogen or hydroxy.

The compound of Formula I or II can have R$^1$, R$^2$, and R$^4$ independently be —(CHR$^{22}$)$_n$—NR$^{20}$R$^{21}$, wherein n is 1 or 2, R$^{20}$ and R$^{21}$ are independently straight or branched C$_4$-C$_{10}$ alkyl, and R$^{22}$ is hydrogen or hydroxy.

The compound of Formula I or II can have R$^1$, R$^2$, and R$^4$ independently be —(CHR$^{22}$)$_n$—NR$^{20}$R$^{21}$, wherein n is 1 or 2, R$^{20}$ and R$^{21}$ are independently butyl, pentyl, hexyl, heptyl, octyl, isopropyl, 2-ethyl hexyl, sec-butyl, or sec-pentyl, and R$^{22}$ is hydrogen or hydroxy.

The compound of Formula I or II can have R$^1$, R$^2$, and R$^4$ independently be —(CHR$^{22}$)$_n$—NR$^{20}$R$^{21}$, wherein n is an integer from 1 to 4, R$^{20}$ and R$^{21}$ are independently alkyl, and R$^{22}$ is hydrogen.

The compound of Formula I or II can have R$^1$, R$^2$, and R$^4$ independently be —(CHR$^{22}$)$_n$—NR$^{20}$R$^{21}$, wherein n is 1 or 2, R$^{20}$ and R$^{21}$ are independently straight or branched C$_4$-C$_{10}$ alkyl, and R$^{22}$ is hydrogen.

The compound of Formula I or II can have R$^1$, R$^2$, and R$^4$ independently be —(CHR$^{22}$)$_n$—NR$^{20}$R$^{21}$, wherein n is 1 or 2, R$^{20}$ and R$^{21}$ are independently butyl, pentyl, hexyl, heptyl, octyl, isopropyl, 2-ethyl hexyl, sec-butyl, or sec-pentyl, and R$^{22}$ is hydrogen.

The compound of Formula I or II can have R$^1$ and R$^2$ independently be substituted C$_1$-C$_{20}$ alkyl.

The compound of Formula I or II can have R$^6$ be hydrogen.

The compound of Formula I or II can have R$^6$ be substituted C$_1$-C$_{10}$ alkyl.

The compound of Formula I or II can have R$^6$ be —S—C$_1$-C$_{12}$ alkyl.

The compound of Formula I or II can have R$^4$ be substituted C$_1$-C$_{20}$ alkyl, or substituted C$_1$-C$_{20}$ aryl.

The compound of Formula I or II can have R$^3$ be hydrogen or unsubstituted C$_1$ to C$_6$ alkyl.

The compound of Formula I or II can have R$^5$ be hydrogen or unsubstituted C$_1$-C$_6$ alkyl.

The compound of Formula II can have the structure of Formula IIA:

IIA wherein R$^7$ and R$^8$ are independently hydrogen or alkyl.

The compound of Formula IIA can have $R^7$ and $R^8$ independently be hydrogen or unsubstituted $C_1$ to $C_6$ alkyl.
The compound of Formula I or II can be selected from the group consisting of:
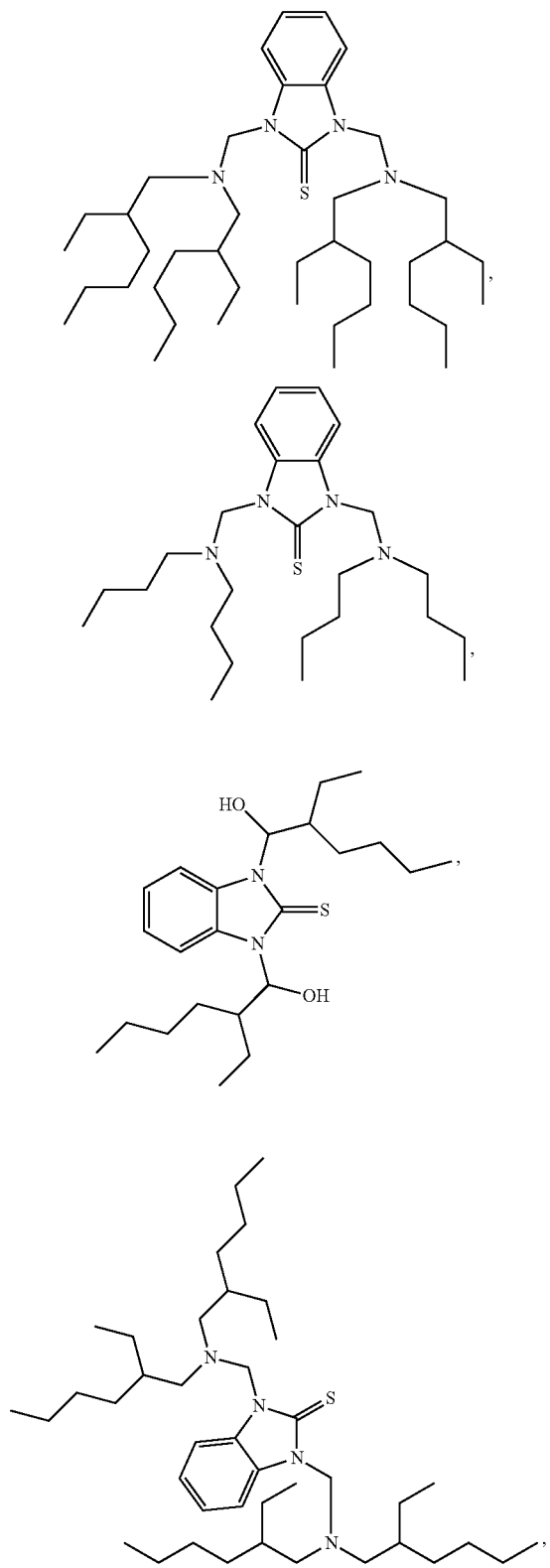
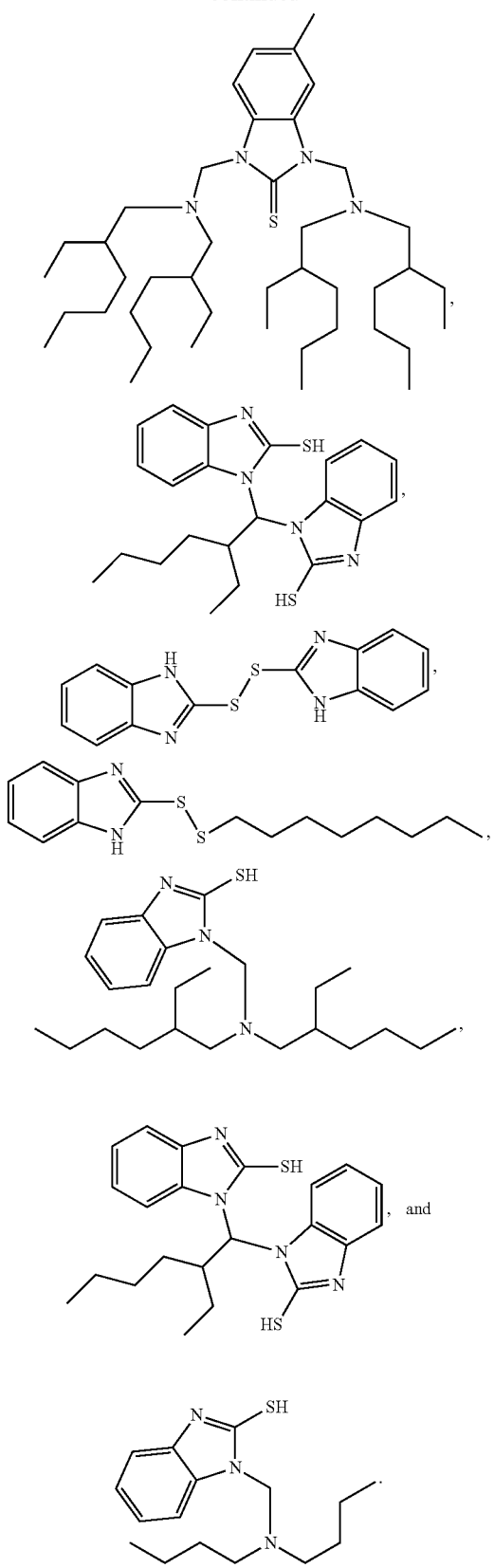
The anticorrosion compound can have the structure of Formula IA

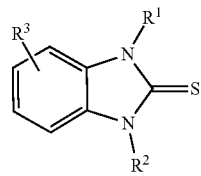

IA wherein $R^1$ and $R^2$ are independently hydrogen or $C_6$ to $C_{30}$ substituted alkyl, where at least one of $R^1$ and $R^2$ are $C_6$ to $C_{30}$ substituted alkyl; and $R^3$ is hydrogen, substituted alkyl, or unsubstituted alkyl.

For the compound of Formula IA, $R^1$ and $R^2$ can independently be $C_6$ to $C_{24}$ substituted alkyl.

For the compound of Formula IA, $R^1$ and $R^2$ can have the structure of Formula IB

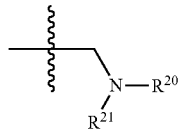

IB wherein $R^{20}$ and $R^{21}$ can independently be hydrogen, substituted alkyl, or unsubstituted alkyl, where at least one of $R^{20}$ and $R^{21}$ can be substituted alkyl or unsubstituted alkyl, and the wavy line indicates the attachment of the substituent to the nitrogen of the ring. For the structure of Formula IB, $R^{20}$ and $R^{21}$ can independently be n-propyl, iso-propyl, n-butyl, iso-butyl, sec-butyl, tert-butyl, n-pentyl, iso-pentyl, sec-pentyl, neo-pentyl, tert-pentyl, n-hexyl, iso-hexyl, sec-hexyl, neo-hexyl, tert-hexyl, n-octyl, iso-octyl, sec-octyl, neo-octyl, tert-octyl, 2-ethylbutyl, 2-ethylpentyl, 2-ethylhexyl, 2-ethylheptyl, 2-ethyloctyl, 3-ethylhexyl, 3-ethylheptyl, or 3-ethyloctyl. Preferably, for the structure of Formula IB, $R^{20}$ and $R^{21}$ can be 2-ethylbutyl or 2-ethylhexyl.

Additionally, the anticorrosion compositions provided herein can be formulated with a solvent to increase solubility within the hydrocarbon-containing liquid.

The solvent can comprise an aromatic solvent, an aliphatic solvent, a nitrogen-containing solvent, a glycol solvent, or a combination thereof.

The aromatic solvent can comprise heavy aromatic naphtha, toluene, kerosene, diesel, gasoline, reformate, or a combination thereof.

The aliphatic solvent can comprise hexane, heptane, octane, or a combination thereof.

The amine-containing solvent can comprise N,N-dimethylformamide, 2-ethylhexylamine, or a combination thereof.

The glycol solvent can comprise triglyme, diglyme, hexylene glycol, or a combination thereof.

The anticorrosion composition can further comprise a compound of Formula III or IV:

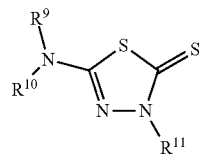

III

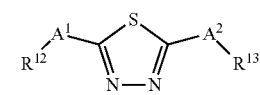

IV wherein $R^9$ and $R^{10}$ are independently hydrogen, substituted alkyl, unsubstituted alkyl, or together form an alkyliminyl; $R^{11}$ is independently substituted alkyl, unsubstituted alkyl, substituted alkenyl, or unsubstituted alkenyl; $R^{12}$ and $R^{13}$ are independently hydrogen, substituted alkyl, unsubstituted alkyl, substituted alkenyl, or unsubstituted alkenyl; $A^1$ and $A^2$ are independently —S—, —N=C—, or —NR$^{14}$; $R^{14}$ is hydrogen, substituted alkyl, or unsubstituted alkyl.

The compound of Formula III or IV can have $R^{11}$ be substituted $C_1$-$C_{12}$ alkyl.

The compound of Formula III or IV can have $R^9$ and $R^{10}$ independently be substituted $C_1$-$C_{20}$ alkyl.

The compound of Formula III or IV can have $R^{12}$ and $R^{13}$ are independently hydrogen, or substituted $C_1$-$C_{25}$ alkyl.

The compound of Formula III or IV can have $R^{11}$ be:

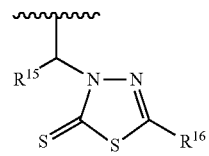

wherein $R^{15}$ is substituted alkyl, or unsubstituted alkyl, $R^{16}$ is —N=CR$^{17}$, or —NR$^{18}$R$^{19}$, wherein $R^{17}$, $R^{18}$, and $R^{19}$ are independently hydrogen, substituted alkyl, unsubstituted alkyl, and the wavy line indicates the attachment of the substituent to the nitrogen of the ring.

The compound of Formula III or IV can be selected from the group consisting of:

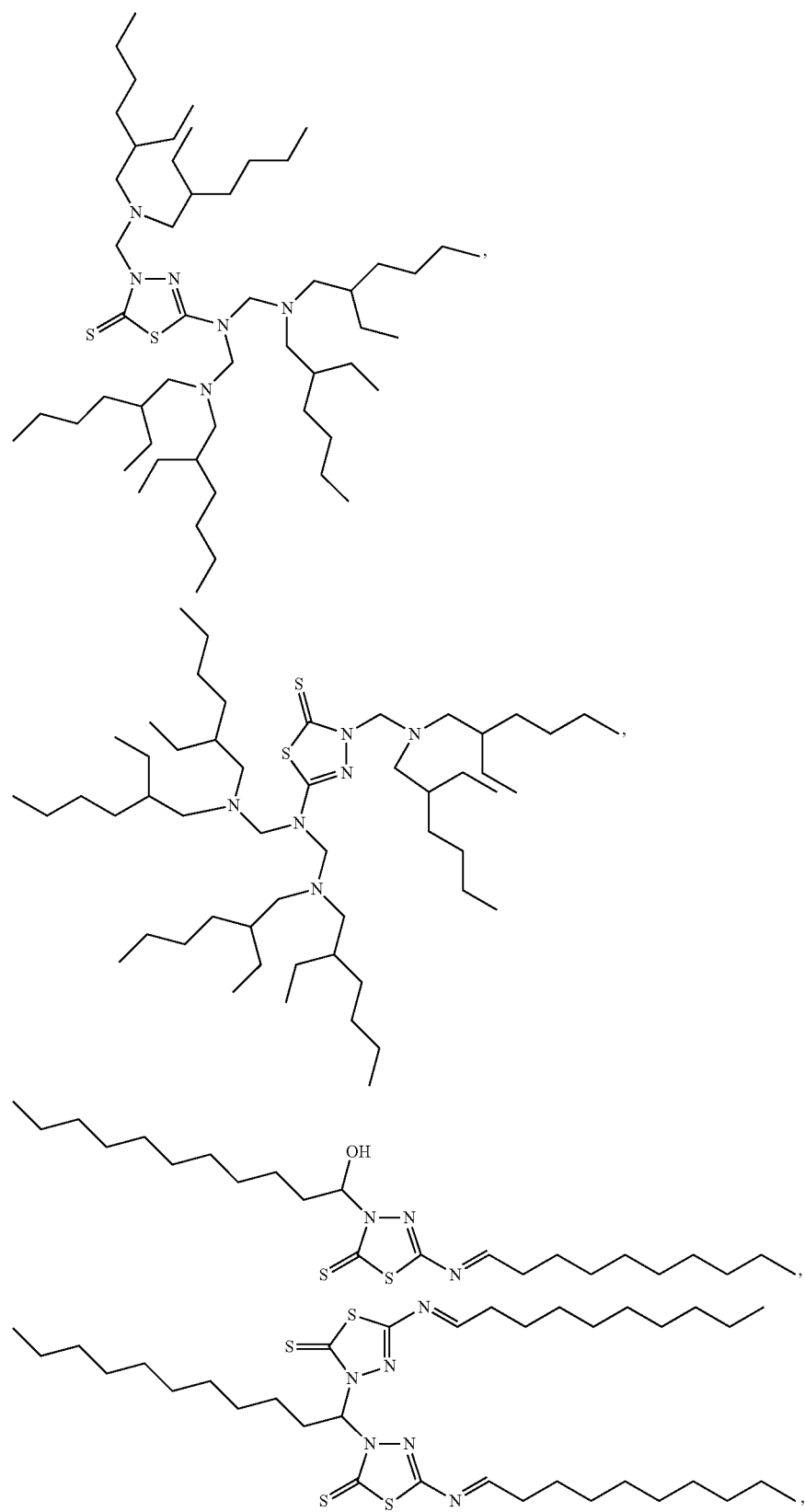

-continued

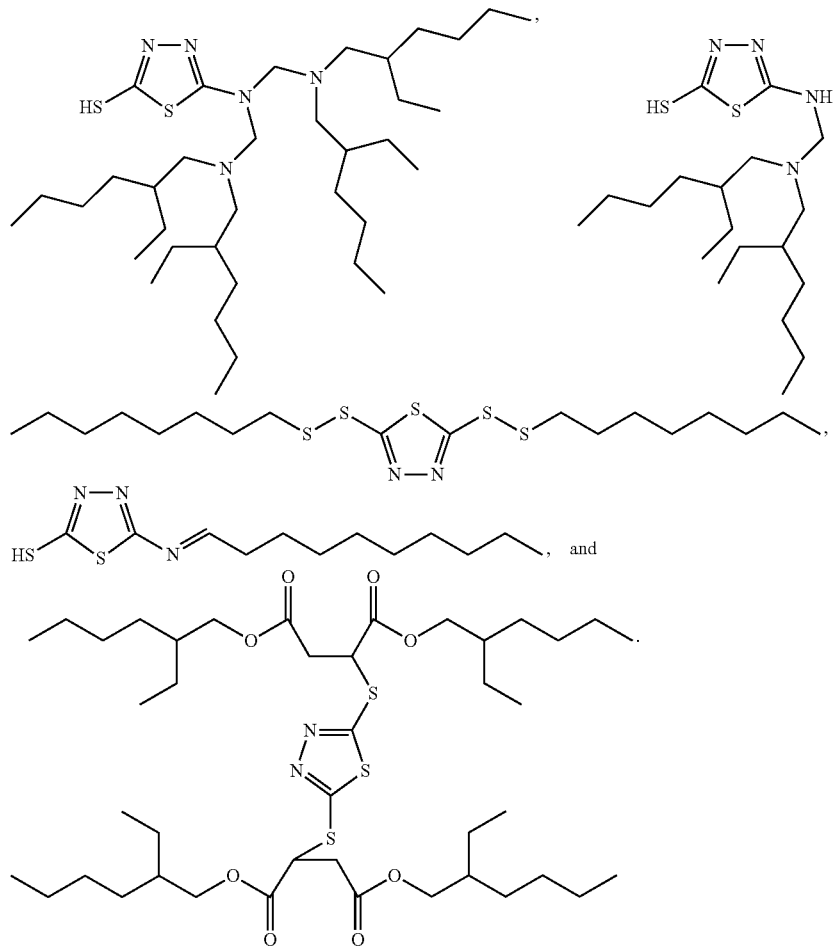

The compound of Formula I or II and the compound of Formula III or IV can be present in the anticorrosion composition at a concentration of from 5 to 95 wt. % and 95 to 5 wt. % respectively, based on the total weight of the formulation. Preferably, the compound of Formula I or II and the compound of Formula III or IV can be present in the anticorrosion composition at a concentration of from 5 to 30 wt. %, and 30 to 5 wt. % respectively, based on the total weight of the formulation.

The metal can comprise silver, copper, or a combination thereof. Preferably, the metal comprises silver.

The hydrocarbon-containing liquid can comprise gasoline, diesel, naphtha, jet fuel, kerosene, or a combination thereof. Preferably, the hydrocarbon-containing liquid can comprise gasoline.

The gasoline can be defined by ASTM D4814 and can meet the EPA's Tier 3 sulfur regulation of less than 10 ppm as an annual average. The gasoline can be produced from atmospheric distillation, alkylation, catalytic hydrocracking, fluid catalytic cracking, thermal cracking, hydro-processing. Hydrocarbons from these sources can also be blended together to form gasoline suitable for our corrosion inhibitor.

The diesel can be defined by ASTM 975 and EN590 and diesel meeting the low and ultra-low sulfur regulations can be used with our corrosion inhibitor.

The kerosene can be defined under ASTM D3699 and the fuel oils can be defined under ASTM D396. Additionally, the hydrocarbon-containing liquid can be petroleum naphtha or straight-run naphtha having a typical boiling range between 68° F. and 428° F. (20° C.-220° C.).

The hydrocarbon-containing fluid can be petroleum fuels and particularly refined hydrocarbon fuels such as gasoline, jet fuel, diesel fuel and kerosene. Other additives that can be added to the petroleum fuels can include ethers used to improve the octane ratings of gasoline. These ethers are typically dialkyl ethers having 1 to 7 carbon atoms in each alkyl group. Illustrative ethers are methyl tertiary-butyl ether, methyl tertiary-amyl ether, methyl tertiary-hexyl ether, ethyl tertiary-butyl ether, n-propyl tertiary-butyl ether, isopropyl tertiary-amyl ether. Mixtures of these ethers and hydrocarbons may also be treated in accordance with the invention.

In gasoline fuels, other fuel additives can be employed with the additive composition employed in the present invention, including, for example, oxygenates, such as t-butyl methyl ether, antiknock agents, such as methylcyclopentadienyl manganese tricarbonyl, and other dispersants/detergents, such as hydrocarbyl amines, or succinimides.

Additionally, antioxidants, metal deactivators, demulsifiers and carburetor or fuel injector detergents can be added to the hydrocarbon-containing liquid.

In diesel fuels, other well-known additives can be employed, such as pour point depressants, flow improvers, cetane improvers, and the like.

The anticorrosion composition can be contacted to the hydrocarbon-containing liquid at a concentration from about 1 ppm to about 100 ppm, from about 1 ppm to about 95 ppm, from about 1 ppm to about 90 ppm, from about 1 ppm to about 85 ppm, from about 1 ppm to about 80 ppm, from about 1 ppm to about 75 ppm, from about 1 ppm to about 70 ppm, from about 1 ppm to about 65 ppm, from about 1 ppm to about 60 ppm, from about 1 ppm to about 55 ppm, from about 1 ppm to about 50 ppm, from about 1 ppm to about 45 ppm, from about 1 ppm to about 40 ppm, from about 1 ppm to about 35 ppm, from about 1 ppm to about 30 ppm, from about 1 ppm to about 25 ppm, from about 1 ppm to about 20 ppm, from about 1 ppm to about 15 ppm, or from about 1 ppm to about 10 ppm.

The composition can comprise an effective amount of the anticorrosion composition described herein and a component selected from the group consisting of an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, and a combination thereof.

The composition can comprise from about 20 to about 90 wt. % of the anticorrosion composition and from about 10 to about 80 wt. % of the component, preferably from about 50 to about 90 wt. % of the anticorrosion composition and from about 10 to about 50 wt. % of the component, and more preferably from about 65 to about 85 wt. % of the anticorrosion composition and from about 15 to about 35 wt. % of the component.

The component of the composition can comprise an organic solvent. The composition can comprise from about 1 to 80 wt. %, from about 5 to 50 wt. %, or from about 10 to 35 wt. % of the one or more organic solvents, based on total weight of the composition. The organic solvent can comprise an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

The component of the composition can comprise an additional corrosion inhibitor. The composition can comprise from about 0.1 to 20 wt. %, 0.1 to 10 wt. %, or 0.1 to 5 wt. % of the corrosion inhibitors, based on total weight of the composition. A composition of the invention can comprise from 0.1 to 10 percent by weight of the corrosion inhibitors, based on total weight of the composition. The composition can comprise 1.0 wt %, 1.5 wt %, 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt %, 8.0 wt %, 8.5 wt %, 9.0 wt %, 9.5 wt %, 10.0 wt %, 10.5 wt %, 11.0 wt %, 11.5 wt %, 12.0 wt %, 12.5 wt %, 13.0 wt %, 13.5 wt %, 14.0 wt %, 14.5 wt %, or 15.0 wt % by weight of the corrosion inhibitors, based on total weight of the composition. Each system can have its own requirements, and the weight percent of one or more additional corrosion inhibitors in the composition can vary with the system in which it is used.

The additional corrosion inhibitor can comprise an imidazoline compound, a quaternary ammonium compound, a pyridinium compound, or a combination thereof.

The additional corrosion inhibitor component can comprise an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (I) or an imidazoline derivative. Representative imidazoline derivatives include an imidazolinium compound of Formula (II) or a bis-quaternized compound of Formula (III).

The additional corrosion inhibitor component can include an imidazoline of Formula (I):

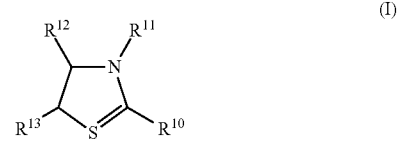

wherein $R^{10}$ is a $C_1$-$C_{20}$ alkyl or a $C_1$-$C_{20}$ alkoxyalkyl group; $R^{11}$ is hydrogen, $C_1$-$C_6$ alkyl, $C_1$-$C_6$ hydroxyalkyl, or $C_1$-$C_6$ arylalkyl; and $R^{12}$ and $R^{13}$ are independently hydrogen or a $C_1$-$C_6$ alkyl group. Preferably, the imidazoline includes an $R^{10}$ which is the alkyl mixture typical in tall oil fatty acid (TOFA), and $R^{11}$, $R^{12}$ and $R^{13}$ are each hydrogen.

The additional corrosion inhibitor component can include an imidazolinium compound of Formula (II):

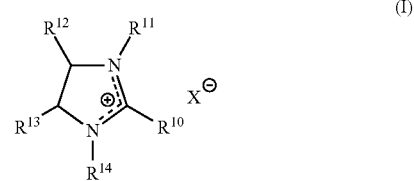

wherein $R^{10}$ is a $C_1$-$C_{20}$ alkyl or a $C_1$-$C_{20}$ alkoxyalkyl group; $R^{11}$ and $R^{14}$ are independently hydrogen, $C_1$-$C_6$ alkyl, $C_1$-$C_6$ hydroxyalkyl, or $C_1$-$C_6$ arylalkyl; $R^{12}$ and $R^{13}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The additional corrosion inhibitor can comprise a bis-quaternized compound having the formula (III):

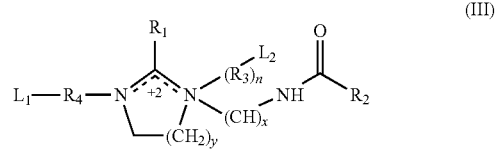

wherein $R_1$ and $R_2$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof; $R_3$ and $R_4$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof; $L_1$ and $L_2$ are each independently absent, H, —COOH, —SO$_3$H, —PO$_3$H$_2$, —COOR$_5$, —CONH$_2$, —CONHR$_5$, or —CON(R$_5$)$_2$; R$_5$ is each independently a branched or unbranched alkyl, aryl, alkylaryl, alkylheteroaryl, cycloalkyl, or heteroaryl group having from 1 to about 10 carbon atoms; n is 0 or 1, and when n is 0, $L_2$ is absent or H; x is from 1 to about 10; and y is from 1 to about 5. Preferably, $R_1$ and $R_2$ are each independently $C_6$-$C_{22}$ alkyl, $C_8$-$C_{20}$ alkyl, $C_{12}$-$C_{18}$ alkyl, $C_{16}$-$C_{18}$ alkyl, or a combination thereof; $R_3$ and $R_4$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1; $R_3$ and $R_4$ are —C$_2$H$_2$—; $L_1$ is —COOH, —SO$_3$H, or —PO$_3$H$_2$; and $L_2$ is absent, H, —COOH, —SO$_3$H, or —PO$_3$H$_2$. For example, $R_1$ and $R_2$ can be derived from a mixture of tall oil fatty acids and are predominantly a mixture of $C_{17}H_{33}$ and $C_{17}H_{31}$ or can be $C_{16}$-$C_{18}$ alkyl; $R_3$ and $R_4$ can be $C_2$-$C_3$ alkylene such as —C$_2$H$_2$—; n is 1 and $L_2$ is —COOH or n is 0 and $L_2$ is absent or H; x is 2; y is 1; $R_3$ and $R_4$ are —C$_2$H$_2$—; and $L_1$ is —COOH.

It should be appreciated that the number of carbon atoms specified for each group of formula (III) refers to the main chain of carbon atoms and does not include carbon atoms that may be contributed by substituents.

The additional corrosion inhibitor can comprise a bis-quaternized imidazoline compound having the formula (III) wherein $R_1$ and $R_2$ are each independently $C_6$-$C_{22}$ alkyl, $C_5$-$C_{20}$ alkyl, $C_{12}$-$C_{18}$ alkyl, or $C_{16}$-$C_{18}$ alkyl or a combination thereof; $R_4$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —SO$_3$H, or —PO$_3$H$_2$; and $L_2$ is absent or H. Preferably, a bis-quaternized compound has the formula (III) wherein $R_1$ and $R_2$ are each independently $C_{16}$-$C_{18}$ alkyl; $R_4$ is —C$_2$H$_2$—; x is 2; y is 1; n is 0; $L_1$ is —COOH, —SO$_3$H, or —PO$_3$H$_2$ and $L_2$ is absent or H.

The corrosion inhibitor can be a quaternary ammonium compound of Formula (IV):

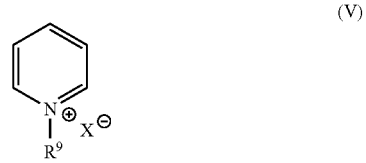

wherein $R_1$, $R_2$, and $R_3$ are independently $C_1$ to $C_{20}$ alkyl, $R_4$ is methyl or benzyl, and X$^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms, and X is Cl, Br or I. For the quaternary salts, R$^{5a}$, R$^{6a}$, R$^{7a}$, and R$^{8a}$ can each be independently selected from the group consisting of alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The additional corrosion inhibitor component can comprise a pyridinium salt such as those represented by Formula (V):

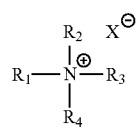

wherein $R^9$ is an alkyl group, an aryl group, or an arylalkyl group, wherein said alkyl groups have from 1 to about 18 carbon atoms and X$^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The additional corrosion inhibitor components can include additional corrosion inhibitors such as phosphate esters, monomeric or oligomeric fatty acids, or alkoxylated amines.

The additional corrosion inhibitor component can comprise a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a more broad distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The additional corrosion inhibitor component can include a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The additional corrosion inhibitor component can comprise an alkoxylated amine. The alkoxylated amine can be an ethoxylated alkyl amine. The alkoxylated amine can be ethoxylated tallow amine.

The component of the composition can comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. The organic sulfur compound can constitute 0.5 to 15 wt. % of the composition, based on total weight of the composition, preferably about 1 to about 10 wt. % and more preferably about 1 to about 5 wt. %. The organic sulfur compound can constitute 1, 2, 3, 4, 5, 6, 7, 8, 9, 10, 11, 12, 13, 14 or 15 wt. % of the composition.

The composition can be substantially free of or free of any organic sulfur compound other than the compound of formula (1). A composition is substantially free of any organic sulfur compound if it contains an amount of organic sulfur compound below the amount that will produce hydrogen sulfide gas upon storage at a temperature of 25° C. and ambient pressure.

The component of the composition can further include a demulsifier.

Preferably, the demulsifier comprises an oxyalkylate polymer, such as a polyalkylene glycol. The demulsifier can constitute from about 0.1 to 10 wt. %, from about 0.5 to 5 wt. %, or from about 0.5 to 4 wt. % of the composition, based on total weight of the composition. The demulsifier can constitute 0.5, 1, 1.5, 2, 2.5, 3, 3.5, 4, 4.5 or 5 wt. % of the composition.

The component of the composition can include an asphaltene inhibitor. The composition can comprise from about 0.1 to 10 wt. %, from about 0.1 to 5 wt. %, or from about 0.5 to 4 wt. % of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The component of the composition can include an additional paraffin inhibitor. The composition can comprise from about 0.1 to 10 wt. %, from about 0.1 to 5 wt. %, or from about 0.5 to 4 wt. % of an additional paraffin inhibitor, based on total weight of the composition. Suitable additional paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The component of the composition can include a scale inhibitor. The composition can comprise from about 0.1 to 20 wt. %, from about 0.5 to 10 wt. %, or from about 1 to 10 wt. % of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The component of the composition can include an emulsifier. The composition can comprise from about 0.1 to 10 wt. %, from about 0.5 to 5 wt. %, or from about 0.5 to 4 wt. % of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkylsaccharide emulsifiers).

The component of the composition can include a water clarifier. The composition can comprise from about 0.1 to 10 wt. %, from about 0.5 to 5 wt. %, or from about 0.5 to 4 wt. % of a water clarifier, based on total weight of the composition. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The component of the composition can include a dispersant. The composition can comprise from about 0.1 to 10 wt. %, from about 0.5 to 5 wt. %, or from about 0.5 to 4 wt. % of a dispersant, based on total weight of the composition. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The component of the composition can include an emulsion breaker. The composition can comprise from about 0.1 to 10 wt. %, from about 0.5 to 5 wt. %, or from about 0.5 to 4 wt. % of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and non-ionic surfactants, and resins, such as phenolic and epoxide resins.

The component of the composition can include a hydrogen sulfide scavenger. The composition can comprise from about 1 to 50 wt. %, from about 1 to 40 wt. %, or from about 1 to 30 wt. % of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The component of the composition can include a gas hydrate inhibitor. The composition can comprise from about 0.1 to 25 wt. %, from about 0.1 to 20 wt. %, or from about 0.3 to 20 wt. % of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The component of the composition can include a kinetic hydrate inhibitor. The composition can comprise from about 5 to 30 wt. %, from about 5 to 25 wt. %, or from about 10 to 25 wt. % of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The component of the composition can include a biocide. The composition can comprise from about 0.1 to 10 wt. %, from about 0.5 to 5 wt. %, or from about 0.5 to 4 wt. % of a biocide, based on total weight of the composition. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

The component of the composition can include a pH modifier. The composition can comprise from about 0.1 to 20 wt. %, from about 0.5 to 10 wt. %, or from about 0.5 to 5 wt. % of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The component of the composition can include a surfactant. The composition can comprise from about 0.1 to 10 wt. %, from about 0.5 to 5 wt. %, or from about 0.5 to 4 wt. % of a surfactant, based on total weight of the composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

Paraffin inhibitor compositions made according to the invention can further include additional functional agents or additives that provide a beneficial property. For example, additional agents or additives can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (i.e., dyes, odorants, perfumes), or other additives suitable for formulation with a corrosion inhibitor composition, and mixtures thereof. Additional agents or additives will vary according to the particular corrosion inhibitor composition being manufactured and its intend use as one skilled in the art will appreciate.

Alternatively, the compositions can not contain any of the additional agents or additives.

Additionally, the anticorrosion compositions can be formulated into a treatment fluid comprising the following components. These formulations include the ranges of the components listed and can optionally include additional agents.

| Component | 1 | 2 | 3 | 4 | 5 | 6 | 7 | 8 | 9 | 10 | 11 | 12 |
|---|---|---|---|---|---|---|---|---|---|---|---|---|
| Anticorrosion composition | 30-90 | 30-90 | 30-90 | 30-90 | 30-90 | 30-90 | 65-85 | 65-85 | 65-85 | 65-85 | 65-85 | 30-90 |
| Organic solvent | 10-35 | | | | | | 10-35 | | | | | 10-35 |
| Corrosion inhibitor | 0.1-20 | 0.1-20 | | | | | 0.1-20 | 0.1-20 | | | | 0.1-20 |
| Asphaltene inhibior | 0.1-5 | 0.1-5 | 0.1-5 | 0.1-5 | | | 0.1-5 | 0.1-5 | 0.1-5 | | | 0.1-5 |
| Paraffin inhibitor | | | | | | | | | | | | |
| Scale inhibitor | 1-10 | 1-10 | 1-10 | 1-10 | 1-10 | | 1-10 | 1-10 | 1-10 | 1-10 | | 1-10 |
| Emulsifier | | | | | | | | | | | | |
| Water clarifier | | | | | | | | | | | | |
| Dispersant | | | | | | | | | | | | |
| Emulsion breaker | | | | | | | | | | | | |
| Gas hydrate inhibitor | | | | | | | | | | | | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | |
| pH modifier | | | | | | | | | | | | |
| Surfactant | | | | | | | | | | | | |

| Component | 13 | 14 | 15 | 16 | 17 | 18 | 19 | 20 | 21 | 22 | 23 | 24 |
|---|---|---|---|---|---|---|---|---|---|---|---|---|
| Anticorrosion composition | 30-90 | 30-90 | 30-90 | 30-90 | 30-90 | 30-90 | 65-85 | 65-85 | 65-85 | 65-85 | 65-85 | 65-85 |
| Organic solvent | | | | | | | | | | | | |
| Corrosion inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Asphaltene inhibior | 0.1-5 | | | | | | 0.1-5 | | | | | |
| Paraffin inhibitor | | | | | | | | | | | | |
| Scale inhibitor | 1-10 | 1-10 | | | 1-10 | | 1-10 | 1-10 | | | | 1-10 |
| Emulsifier | | | | | | | | | | | | |
| Water clarifier | | | | | | | | | | | | |
| Dispersant | | | | | | | | | | | | |
| Emulsion breaker | | | | | | | | | | | | |
| Gas hydrate inhibitor | 0.1-25 | 0.1-25 | 0.1-25 | | | | 0.1-25 | 0.1-25 | 0.1-25 | | 0.1-25 | |
| Biocide | | | | | | 0.5-5 | 0.5-5 | 0.5-5 | 0.5-5 | 0.5-5 | | |
| pH modifier | | | | | | | | | | | | |
| Surfactant | | | | | | | | | | | | |

The compositions can be prepared by combining the components as described above.

The compositions can be used for reducing, inhibiting or preventing corrosion of a metal surface used in recovery, transportation, refining or storage of a hydrocarbon fluid containing elemental sulfur or polysulfide. The method comprises contacting any of the compositions described herein with the metal surface to reduce, inhibit or prevent corrosion of the metal surface.

The compositions can be used for inhibiting corrosion by treating the hydrocarbon fluid containing elemental sulfur or polysulfide with an effective amount of the composition, such as, for example, a concentration of about 1 to about 10,000 ppm of the composition in the hydrocarbon fluid.

The compositions can be used in any industry where it is desirable to inhibit corrosion from a metal surface which comes in contact with the hydrocarbon fluid.

The hydrocarbon fluid can be any type of liquid hydrocarbon including, but are not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. The fluid can be a refined hydrocarbon product.

The composition can be added to the hydrocarbon fluid before the hydrocarbon fluid contacts the metal surface.

The hydrocarbon fluid can contain elemental sulfur, a polysulfide, hydrogen sulfide, mercaptans, or a combination thereof. The hydrocarbon fluid can contain 10, 20, 30, 40, 50, 60, 70, 80, 90, 100, 200, 300, 400, 500, 600, 700, 800, 900 1,000 or more ppm of elemental sulfur and/or 10, 20, 30, 40, 50, 60, 70, 80, 90, 100, 200, 300, 400, 500, 600, 700, 800, 900 1,000 or more ppm of a polysulfide, such as sodium tetrasulfide.

The compositions can be used in water systems, condensate/oil systems/gas systems, or any combination thereof. The compositions can be applied to a gas or liquid produced, or used in the production, transportation, storage, refining and/or separation of crude oil or natural gas. The compositions can be applied to a gas stream used or produced in a coal-fired process, such as a coal-fired power plant. The compositions can be applied to a gas or liquid produced or used in a waste-water process, a farm, a slaughter house, a land-fill, a municipality waste-water plant, a coking coal process, or a biofuel process.

A fluid to which the compositions can be introduced can be an aqueous medium. The aqueous medium can comprise water, gas, and optionally liquid hydrocarbon. A fluid to which the compositions can be introduced can be a liquid hydrocarbon.

A fluid or gas treated with the composition can be at any selected temperature, such as ambient temperature or an elevated temperature. The fluid (e.g., liquid hydrocarbon) or gas can be at a temperature of from about 40° C. to about 250° C. The fluid or gas can be at a temperature of from −50° C. to 300° C., 0° C. to 200° C., 10° C. to 100° C., or 20° C. to 90° C. The fluid or gas can be at a temperature of −50° C., −45° C., −40° C., −35° C., −30° C., −25° C., −20° C., −15° C., −10° C., −5° C., or 0° C. The fluid or gas can be found in an arctic environment, and can have a temperature and salinity typical of such environment.

The compositions of the invention can be added to a fluid at various levels of water cut. For example, the water cut can be from 0% to 100% volume/volume (v/v), from 1% to 80% v/v, from 1% to 75% v/v, from 1% to 70% v/v, from 1% to 65% v/v, or from 1% to 60% v/v.

The fluid can be an aqueous medium that contains various levels of salinity. The fluid can have a salinity of from about 0% to 25% w/w, from about 1% to 25% w/w, from about 2% to about 25% w/w, from about 5% to about 25% w/w, or from about 10% to about 25% weight/weight (w/w) total dissolved solids (TDS).

The fluid or gas in which the composition is introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The composition can be introduced to large diameter flow lines of from about 1 inch to about 4 feet in diameter, small gathering lines, small flow lines and headers. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units. The fluid or gas can be contained in water systems, condensate/oil systems/gas systems, or any combination thereof.

The composition can be introduced into a fluid or gas by any appropriate method for ensuring dispersal through the fluid or gas. The composition can be added at a point in a flow line upstream from the point at which corrosion prevention is desired. The compositions can be injected using mechanical equipment such as chemical injection pumps, piping tees, injection fittings, atomizers, quills, and the like.

The composition can be pumped into an oil and/or gas pipeline using an umbilical line. A capillary injection system can be used to deliver the composition to a selected fluid. The compositions can be introduced into a liquid and mixed. The composition can be injected into a gas stream as an aqueous or non-aqueous solution, mixture, or slurry. The fluid or gas can be passed through an absorption tower comprising the composition.

The composition can be applied to a hydrocarbon fluid to provide any selected concentration. In practice, the composition is typically added to a flow line to provide an effective treating dose of from about 100 ppm to about 1,000,000 ppm, from about 100 ppm to about 500,000 ppm, from about 100 ppm to about 200,000 ppm, from about 100 ppm to about 100,000 ppm, from about 100 ppm to about 80,000 ppm, from about 100 ppm to about 60,000 ppm, from about 100 ppm to about 50,000 ppm, from about 100 ppm to about 40,000 ppm, from about 100 ppm to about 30,000 ppm, from about 100 ppm to about 20,000 ppm, from about 100 ppm to about 10,000 ppm, from about 500 to about 100,000 ppm, from about 500 to about 80,000 ppm, from about 500 to about 60,000 ppm, from about 500 to about 50,000 ppm, from about 500 to about 40,000 ppm, from about 500 to about 30,000 ppm, from about 500 to about 20,000 ppm, or from about 500 to about 10,000 ppm. Each system can have its own requirements, and the effective amount of a composition to sufficiently reduce the rate of corrosion can vary with the system in which it is used.

The compositions can be applied continuously, in batch, or a combination thereof. For example, the composition doses can be continuous to prevent corrosion or intermittent (i.e., batch treatment). The composition doses can be continuous/maintained and/or intermittent to inhibit corrosion. Dosage rates for continuous treatments typically range from about 10 to about 5,000 ppm. Dosage rates for batch treatments typically range from about 500 to about 10,000 ppm. The composition can also be applied as a pill to a pipeline, providing a high dose (e.g., up to 1,000,000 ppm) of the composition.

The flow rate of a flow line in which the composition is used can be between 0 and 100 feet per second, or between 0.1 and 50 feet per second. The compositions can be formulated with water in order to facilitate addition to the flow line.

The compositions can be added to the circulation line that is fed to the finished fuel tank in the refinery.

Various compounds of Formula 1A can be prepared by reacting 2-Mercaptobenzimidazole with an amine at a molar ratio of from about 2:1 to 1:3 in a round bottom flask. A solvent (e.g., toluene or heavy aromatic naphtha (HAN) is added, followed by the drop wise addition of formalin at a 1:2 to 2:1 molar ratio of formalin to amine. The reaction is stirred overnight at room temperature. The reaction mixture is then poured into a separatory funnel and the organic layer is collected and dried with $Na_2SO_4$ to yield the resulting product as 50% active in solution.

The general reaction scheme is:

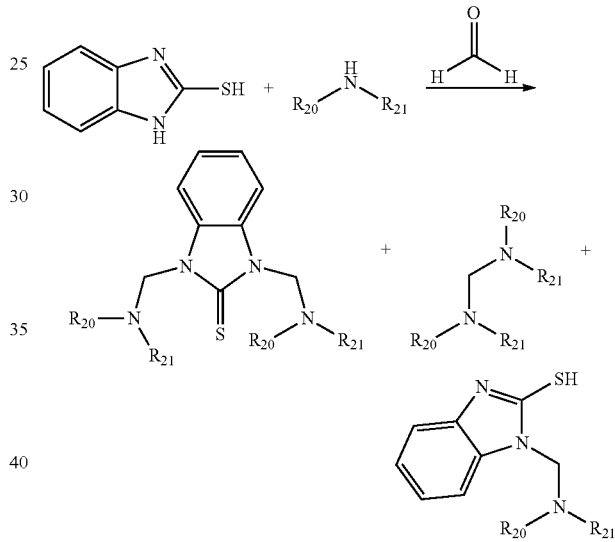

wherein $R_{20}$ and $R_{21}$ are as defined above.

DEFINITIONS

Unless otherwise indicated, an alkyl group as described herein alone or as part of another group is an optionally substituted linear saturated monovalent hydrocarbon substituent containing from one to thirty carbon atoms and preferably one to thirty carbon atoms in the main chain or one to twenty carbon atoms in the main chain, or an optionally substituted branched saturated monovalent hydrocarbon substituent containing three to thirty carbon atoms, and preferably three to twenty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

Unless otherwise indicated, an alkenyl group as described herein alone or as part of another group are preferably lower alkenyl containing from two to eight carbon atoms in the principal chain and up to 20 carbon atoms. They may be straight chain, branched chain, or cyclic and include ethenyl, propenyl, isopropenyl, butenyl, isobutenyl, hexenyl, and the like.

The term "aryl" as used herein alone or as part of another group denotes an optionally substituted monovalent aromatic hydrocarbon radical, preferably a monovalent monocyclic or bicyclic group containing from 6 to 12 carbons in the ring portion, such as phenyl, biphenyl, naphthyl, substituted phenyl, substituted biphenyl or substituted naphthyl. Phenyl and substituted phenyl are the more preferred aryl groups. The term "aryl" also includes heteroaryl.

The term "hydrocarbon" as used herein describes a compound or substituent consisting exclusively of the elements carbon and hydrogen.

The term "substituted" as in "substituted alkyl," "substituted alkenyl," and the like, means that in the group in question (i.e., the alkyl, alkenyl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino (—N($R_A$)($R_B$), wherein $R_A$ and $R_B$ are independently hydrogen, alkyl, aryl, cycloalkyl, or heterocyclo), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

The term "heterocyclo," as used herein alone or as part of another group, denotes a saturated or unsaturated monovalent monocyclic group of 4 to 8 ring atoms in protonated or unprotonated form, in which one or two ring atoms are heteroatom(s), independently selected from N, O, and S, and the remaining ring atoms are carbon atoms. Additionally, the heterocyclic ring may be fused to a phenyl or heteroaryl ring, provided that the entire heterocyclic ring is not completely aromatic. Exemplary heterocyclo groups include the heteroaryl groups described above, pyrrolidino, pyrrolidinium, piperidino, piperidinium, morpholino, morpholinium, piperazino, piperazinium, benzimidazole, thiobenzimidazole, benzoxazole, benzothiazole, mercaptobenzimidazole, and the like.

Having described the invention in detail, it will be apparent that modifications and variations are possible without departing from the scope of the invention defined in the appended claims.

EXAMPLES

The following non-limiting examples are provided to further illustrate the present invention.

All chemicals and reagents were purchased from Sigma-Aldrich (St. Louis, Mo.) unless otherwise noted.

Example 1: Sulfur Content Determination

The sulfur content (mass %) for the major products described by the reaction schemes shown in Examples 2-9, below, were calculated based on the total molecular weight of sulfur divided by the molecular weight of the molecule. The calculated sulfur content is listed above the major product within parentheticals.

The calculated sulfur content of two starting reagents, 1,3,4-thiadiazole-2-5-dithiol and 5-amino-1,3,4-thiadiazole-2-thiol, are 64 and 48, respectively.

The sulfur content for the blends, described in Example 10, below, were submitted for X-ray fluorescence (XRF) analysis.

Example 2: Synthesis of Incumbent 1,3,4-Thiadiazole-2,5-thiol (7.0 g, 46.7 mmoles) was mixed with octane-1-thiol (14.6 g, 93.3 mmoles) in heavy aromatic naphtha (HAN) (20.6 mL) in a 500 mL round bottom flask. Water (25 mL) was added to the resulting reaction, followed by the drop wise addition of 30% hydrogen peroxide (10.6 g, 93.3 mmoles). The reaction was stirred overnight at 80° C. The HAN layer was passed through CELITE which had a thin layer of $Na_2SO_4$ to yield the resulting product (45.31 g) as 50% active in solution.

The reaction products are identified hereinafter as Product A. This product is commercially available from Nalco Champion.

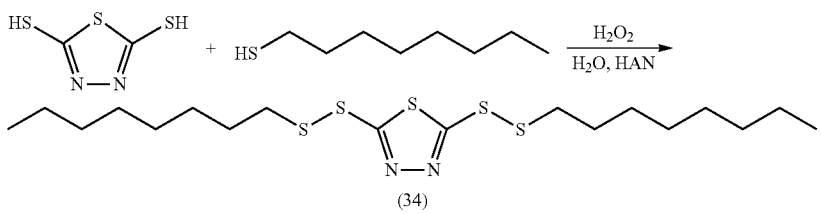

(34)

Example 3: Synthesis of 2-Mercaptobenzimidazole Alkyl Derivatives

2-Mercaptobenzimidazole (10 g, 66.58 mol) was added to bis(2-ethylhexyl)amine (32.16 g, 133.2 mmoles) in a 500 mL round bottom flask. Toluene (46.14 g) was added, followed by the drop wise addition of formalin (4.0 g, 133.2 mmoles). The reaction was stirred overnight at room temperature. The reaction mixture was poured into a separatory funnel and the organic layer was collected and dried with $Na_2SO_4$ to yield the resulting product (86.6 g) as 50% active in solution.

The reaction can also be performed in a similar amount of HAN instead of toluene.

The reaction products are identified hereinafter as Product B.

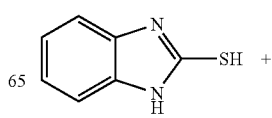

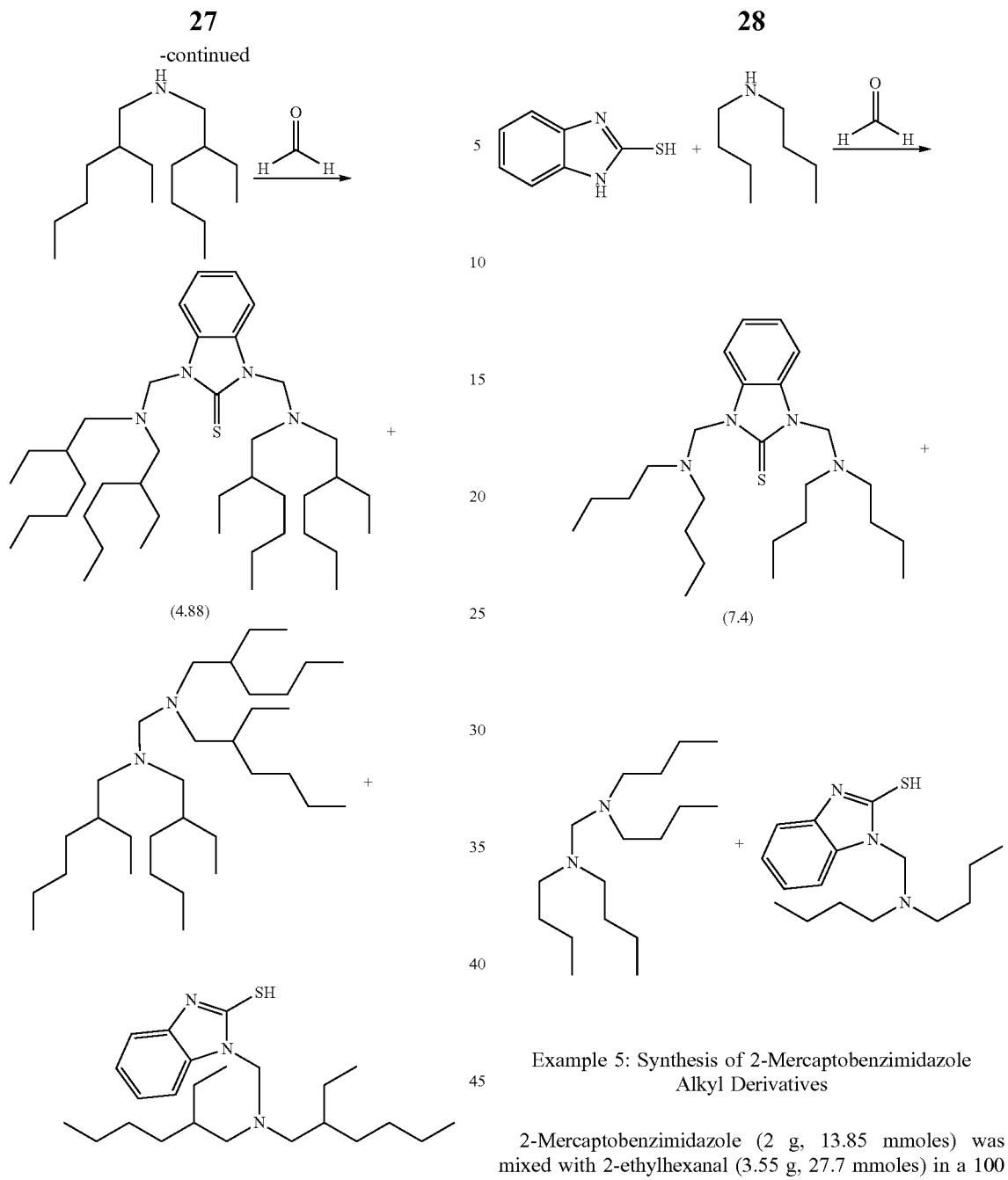

Example 4: Synthesis of 2-Mercaptobenzimidazole Alkyl Derivatives

2-Mercaptobenzimidazole (10 g, 66.58 mmoles) was added to dibutylamine (17.2 g, 133.2 mmoles) in a 500 mL round bottom flask. Toluene (46.14 g) was added, followed by the drop wise addition of formalin (4.0 g, 133.2 mmoles). The reaction was stirred overnight at room temperature. The reaction mixture was poured into a separatory funnel and the organic layer was collected and dried with $Na_2SO_4$ to yield the resulting product (86.6 g) as 50% active in solution.

The reaction can also be performed in a similar amount of HAN instead of toluene.

The reaction products are identified hereinafter as Product C.

Example 5: Synthesis of 2-Mercaptobenzimidazole Alkyl Derivatives

2-Mercaptobenzimidazole (2 g, 13.85 mmoles) was mixed with 2-ethylhexanal (3.55 g, 27.7 mmoles) in a 100 mL round bottom flask. Triglyme (10 mL) was added and the resulting reaction was heated at 90° C. until the solution became clear. The reaction mixture was then cooled and collected to give the resulting product (15.1 g) as 35% active in solution.

The reaction products are identified hereinafter as Product D.

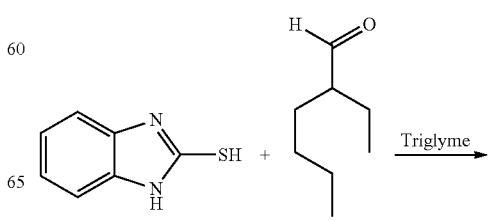

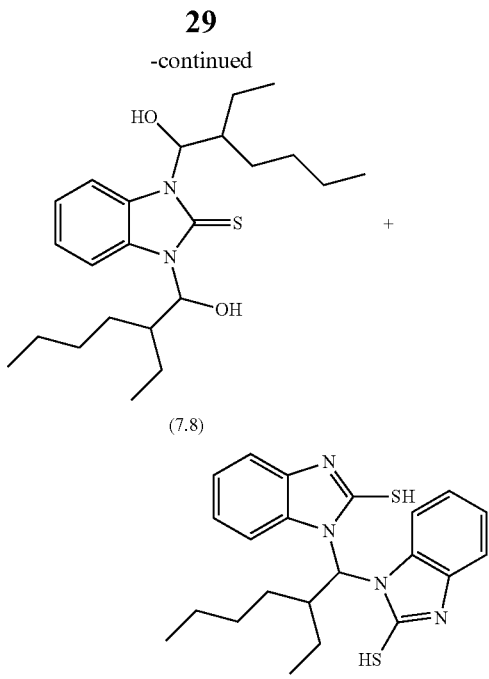

(7.8)

Example 6: Synthesis of 2-Mercaptobenzimidazole Disulfide Derivatives

2-Mercaptobenzimidazole (2.0 g, 13.3 mmoles) was mixed with octane-1-thiol (1.94 g, 13.3 mmoles) in toluene (5.9 mL) in a 100 mL round bottom flask. Water (7 mL) was added to the resulting reaction followed by the drop wise addition of a 35% hydrogen peroxide solution (1.51 g, 13.3 mmoles). The resulting reaction was stirred overnight at 80° C. The toluene layer was passed through CELITE which had a thin layer of $Na_2SO_4$ to yield the resulting product (45.31 g) as 50% active in solution.

The reaction product is identified hereinafter as Product E.

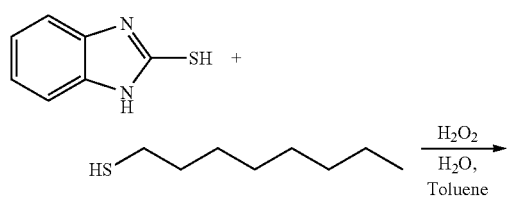

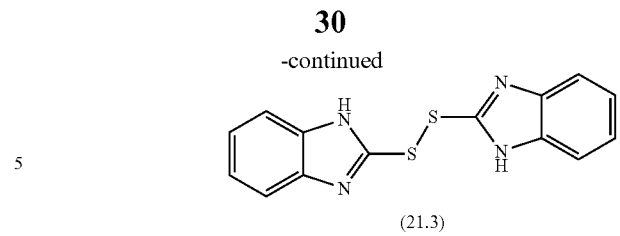

(21.3)

Thiourea (1.24 g, 16.25 mmoles) was dissolved in MeOH (10 mL) and HCl (0.8 mL) was added in a 100 mL round bottom flask. The resulting mixture was stirred overnight followed by the addition of HAN (10 mL), 2-mercaptobenzimidazole (3.2 g, 21.1 mmoles) and octane-1-thiol (3.1 g, 21.1 mmoles). Water (7 mL) was added to the reaction mixture followed by the drop wise addition of 35% hydrogen peroxide (2.27 mL, 21.1 mmoles). The reaction was stirred for an additional 18 hours at room temperature. The reaction mixture was quenched by the addition of $NaHCO_3$. The HAN layer was passed through CELITE which had a thin layer of $Na_2SO_4$ to yield the resulting product (17.6 g) as 30% active in solution.

The reaction product is identified hereinafter as Product F.

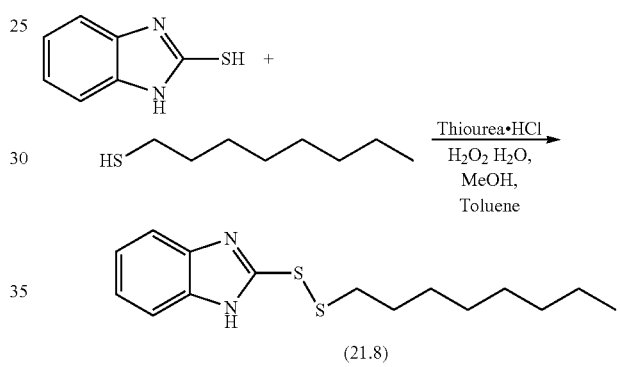

(21.8)

Example 7: Synthesis of Thiadiazole Alkyl Derivatives

5-Amino-1,3,4-thiadiazole-2-thiol (2.15 g, 14.7 mmoles) was added to bis-2-ethylhexylamine (10.6 g, 44.1 mmoles) in a 250 mL round bottom flask. Triglyme (15 mL) was added, followed by the drop wise addition of formalin (3.6 g, 44.1 mmoles). The reaction was stirred overnight at room temperature. The reaction mixture was poured into a separatory funnel and the organic layer was collected and dried with $Na_2SO_4$ to yield the resulting product (29 g) as 50% active in solution.

The reaction products are identified hereinafter as Product G.

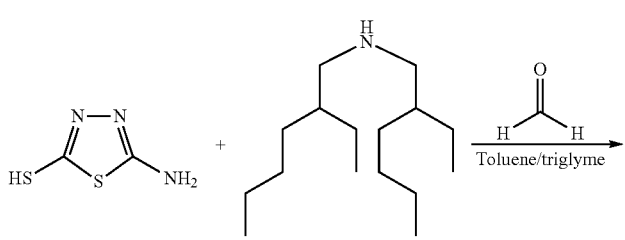

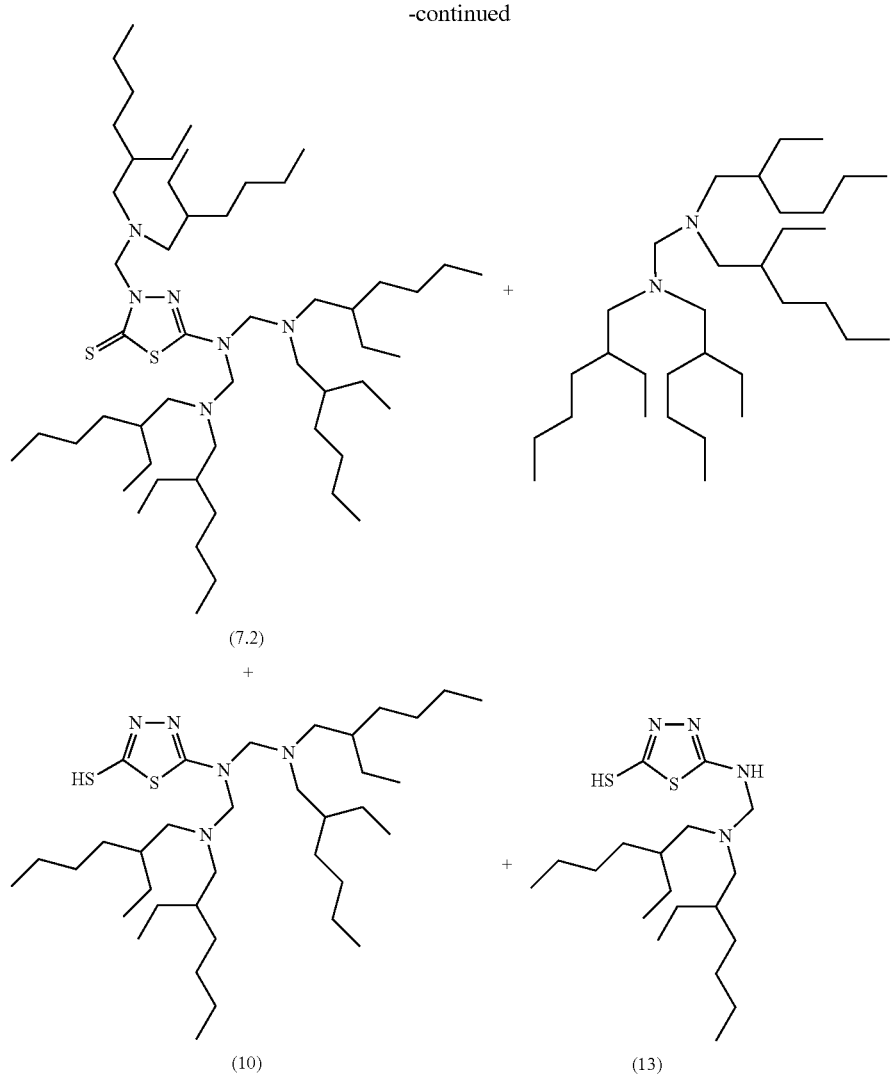

(7.2)

(10)     (13)

Example 8: Synthesis of Thiadiazole Alkene Derivatives

5-Amino-1,3,4-thiadiazole-2-thiol (1.08 g, 7.2 mmoles) was mixed with decanal (3.37 g, 27.7 mmoles) in a 100 mL round bottom flask. Triglyme (5 mL) was added and the resulting reaction was stirred for 7 hours at 90° C. The reaction mixture was then cooled and collected to yield the resulting product (8.9 g) as 50% active in solution.

The reaction products are identified hereinafter as Product H.

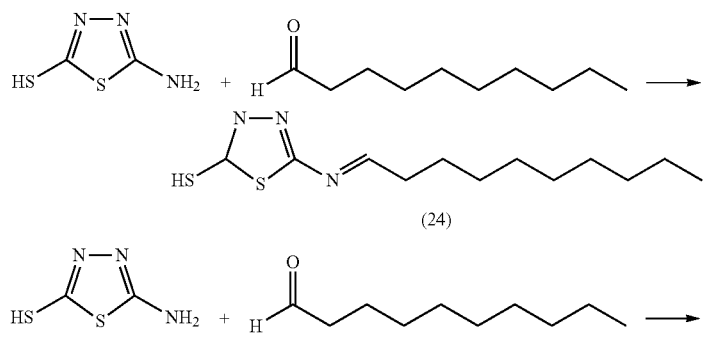

(24)

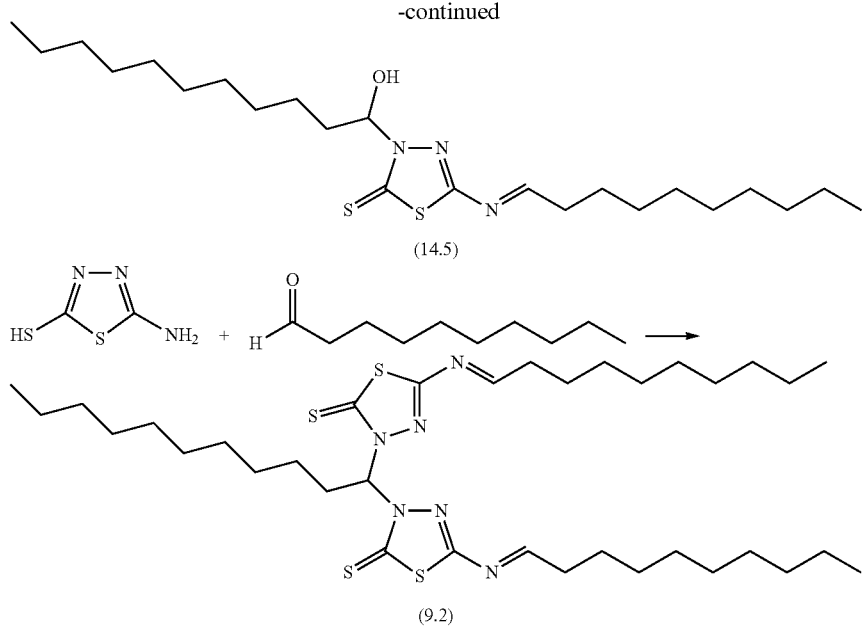

Example 9: Synthesis of Thiadiazole Maleate Derivatives

5-Amino-1,3,4-thiadiazole-2-thiol (1.56 g, 11.78 mmoles) was mixed with decanal (3.37 g, 27.7 mmoles) in a 100 mL round bottom flask. Triglyme (5 mL) was added. The reaction was stirred for 7 hours at 90° C. The reaction mixture was then cooled and collected to yield the resulting product (8.9 g) as 50% active in solution.

The reaction product is identified hereinafter as Product I.

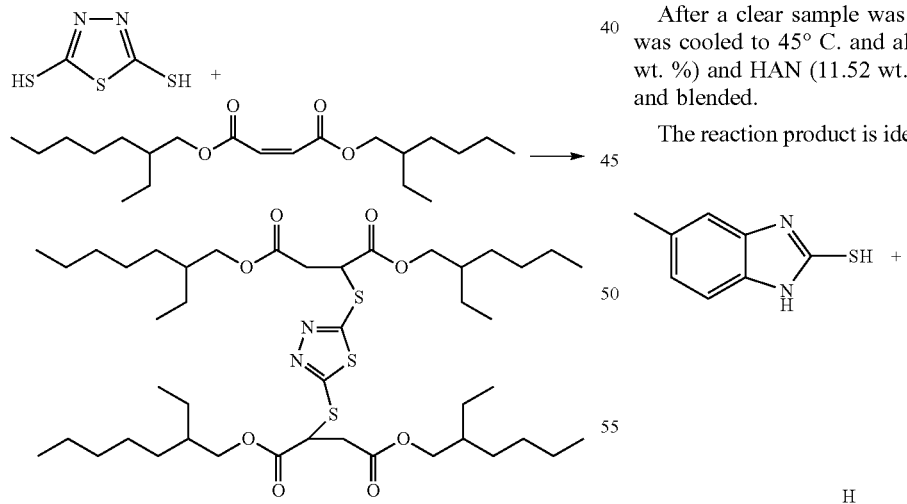

Example 10: Synthesis of 2-Mercaptobenzimidazole Alkyl Derivatives

5-Methyl-2-mercaptobenimidzole (20.00 g, 0.122 moles), di-(2-ethylhexyl)amine (61.76 g, 0.256 moles), HAN (121.80 g, 57 wt. %), and paraformaldehyde (7.94 g, 0.243 moles) were mixed in a 500 mL round bottom flask. The reaction mixture was stirred for 4 hours at 90° C. During this time the mixture clarified and water was generated. A sample was removed and examined for clarity at 25 and 0° C. The sample was not clear and thus failed.

The reaction temperature was increased to 105° C. and a nitrogen sweep was applied to remove any water that had been generated. Samples were removed every 30 minutes and monitored for clarity at 25 and 0° C. Samples collected after approximately 1 hour or when approximately 5.6 wt. % condensate, i.e., water, had been removed passed, i.e., the samples were clear.

After a clear sample was obtained, the reaction mixture was cooled to 45° C. and alkyl mercapto-thiadiazole (24.6 wt. %) and HAN (11.52 wt. %) were added to the mixture and blended.

The reaction product is identified hereinafter as Product J.

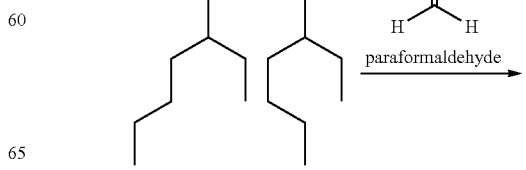

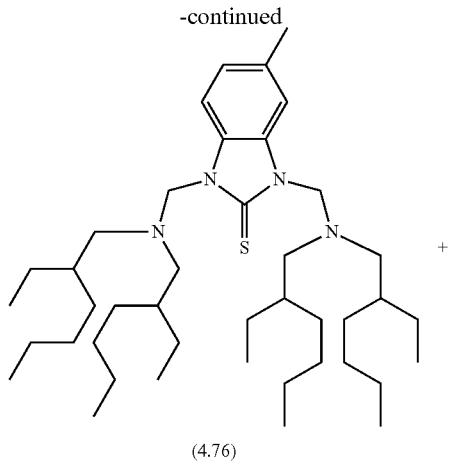

(4.76)

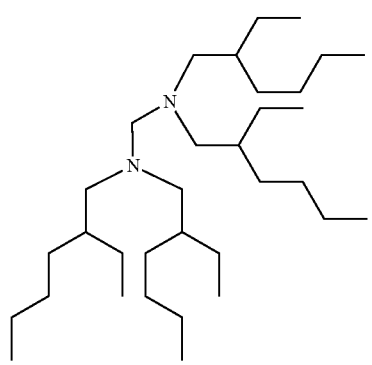

Example 11: Preparation of Product Blends

Product A (5 g of 50% active in HAN) was mixed with product B (5 g of 50% active in HAN) to give 10 grams 50% active product. The product blend is identified hereinafter as Product K.

Product A (5 g of 50% active in HAN) was mixed with product J (5 g of 50% active in HAN) to give 10 grams 50% active product I. The product blend is identified hereinafter as Product L.

Example 12: Silver Corrosion Tests

A modified Corrosiveness to Silver by Automotive Spark Method ASTM D7671 was conducted using silver wool and silver strips suspended in gasoline or isooctane. The corrosion tests were performed in both a pressure and open air vessel, however, the results were similar so the results performed in a closed vessel are shown below. Products as described in Examples 3-11, above, were compared as corrosion inhibitors against the incumbent, described in Example 2.

The result of the test is based on a visual rating that is classified as an integer in the range from 0 to 4 with 0 indicating no tarnish, 1 indicating slight tarnish, 2 indicating moderate tarnish, 3 indicating slight blackening, and 4 indicating blackening. Values of 0-1 are considered a pass and 2-4 are considered a fail.

TABLE 1

Performance of Product B in Comparison to the Incumbent, Product A.

| Fluid | Metal | Product | Dosage (ppm) | Results |
|---|---|---|---|---|
| Isooctane | Silver wool | Blank | — | 4 |
| Isooctane | Silver wool | A | 2 | 0 |
| Isooctane | Silver wool | B | 2 | 2 |
| Isooctane | Silver wool | B | 4 | 1 |
| Isooctane | Silver wool | B | 8 | 0 |
| Isooctane | Silver wool | B | 12 | 0 |
| Gasoline | Silver wool | Blank | — | 4 |
| Gasoline | Silver wool | A | 5 | 0 |
| Gasoline | Silver wool | B | 10 | 0 |
| Gasoline | Silver wool | B | 20 | 0 |
| Gasoline | Silver strips | Blank | — | 4 |
| Gasoline | Silver strips | A | 5 | 0 |
| Gasoline | Silver strips | B | 10 | 0 |
| Gasoline | Silver strips | B | 20 | 0 |

TABLE 2

Performance of Product C in Comparison to the Incumbent, Product A.

| Fluid | Metal | Product | Dosage (ppm) | Results |
|---|---|---|---|---|
| Gasoline | Silver wool | Blank | — | 4 |
| Gasoline | Silver wool | A | 5 | 0 |
| Gasoline | Silver wool | C | 5 | 0 |
| Gasoline | Silver wool | C | 10 | 0 |
| Gasoline | Silver wool | C | 15 | 0 |
| Gasoline | Silver wool | B | 20 | 0 |

TABLE 3

Performance of Product D in Comparison to the Incumbent, Product A.

| Fluid | Metal | Product | Dosage (ppm) | Results |
|---|---|---|---|---|
| Gasoline | Silver wool | Blank | — | 4 |
| Gasoline | Silver wool | A | 2 | 3 |
| Gasoline | Silver wool | I | 5 | 1 |
| Gasoline | Silver wool | D | 5 | 0 |
| Gasoline | Silver wool | D | 10 | 0 |
| Gasoline | Silver wool | D | 15 | 0 |
| Gasoline | Silver wool | C | 20 | 0 |

TABLE 4

Performance of Products E and F in Comparison to the Incumbent, Product A.

| Fluid | Metal | Product | Dosage (ppm) | Results |
|---|---|---|---|---|
| Gasoline | Silver wool | Blank | — | 4 |
| Gasoline | Silver wool | A | 5 | 0 |
| Gasoline | Silver wool | E | 5 | 4 |
| Gasoline | Silver wool | E | 10 | 4 |
| Gasoline | Silver wool | E | 30 | 1 |
| Gasoline | Silver wool | F | 30 | 1 |

TABLE 5

Performance of Product G in Comparison to the Incumbent, Product A.

| Fluid | Metal | Product | Dosage (ppm) | Results |
|---|---|---|---|---|
| Gasoline | Silver wool | Blank | — | 4 |
| Gasoline | Silver wool | A | 10 | 1 |
| Gasoline | Silver wool | G | 5 | 1 |
| Gasoline | Silver wool | G | 10 | 0 |
| Gasoline | Silver wool | G | 15 | 0 |
| Gasoline | Silver wool | G | 20 | 0 |

TABLE 6

Performance of Products H and H blended with the Incumbent, Product A, in Comparison to the Incumbent.

| Fluid | Metal | Product | Dosage (ppm) | Results |
|---|---|---|---|---|
| Gasoline | Silver wool | Blank | — | 4 |
| Gasoline | Silver wool | A | 5 | 1 |
| Gasoline | Silver wool | H | 5 | 0 |
| Gasoline | Silver wool | H | 10 | 0 |
| Gasoline | Silver wool | H + A (1:1) | ? | 0 |

TABLE 7

Performance of Product I in Comparison to the Incumbent, Product A.

| Fluid | Metal | Product | Dosage (ppm) | Results |
|---|---|---|---|---|
| Gasoline | Silver wool | Blank | — | 4 |
| Gasoline | Silver wool | A | 5 | 0 |
| Gasoline | Silver wool | I | 10 | 0 |
| Gasoline | Silver wool | I | 15 | 0 |

TABLE 8

Performance of the Product J in Comparison to the Incumbent, Product A.

| Fluid | Metal | Product | Dosage (ppm) | Results |
|---|---|---|---|---|
| Gasoline | Silver wool | Blank | — | 2 |
| Gasoline | Silver wool | A | 2 | 0 |
| Gasoline | Silver wool | J | 1 | 2 |
| Gasoline | Silver wool | J | 2 | 0 |

TABLE 9

Performance of the Product K in Comparison to the Incumbent, Product A.

| Fluid | Metal | Product | Dosage (ppm) | Results |
|---|---|---|---|---|
| Gasoline | Silver wool | Blank | — | 4 |
| Gasoline | Silver wool | A | 2 | 4 |
| Gasoline | Silver wool | A | 5 | 0 |
| Gasoline | Silver wool | A | 5 | 0 |
| Gasoline | Silver wool | A | 5 | 4 |
| Gasoline | Silver wool | A | 5 | 1 |
| Gasoline | Silver wool | A | 10 | 2 |
| Gasoline | Silver wool | A | 10 | 0 |
| Gasoline | Silver wool | A | 10 | 1 |
| Gasoline | Silver wool | B | 10 | 4 |
| Gasoline | Silver wool | B | 20 | 0 |
| Gasoline | Silver wool | K | 2 | 0 |
| Gasoline | Silver wool | K | 5 | 0 |
| Gasoline | Silver wool | K | 5 | 1 |
| Gasoline | Silver wool | K | 10 | 0 |
| Gasoline | Silver wool | K | 10 | 0 |
| Gasoline | Silver wool | K | 10 | 0 |
| Gasoline | Silver strips | Blank | — | 4 |
| Gasoline | Silver strips | A | 2 | 3 |
| Gasoline | Silver strips | A | 4 | 0 |
| Gasoline | Silver strips | A | 5 | 1 |
| Gasoline | Silver strips | A | 6 | 0 |
| Gasoline | Silver strips | A | 8 | 0 |
| Gasoline | Silver strips | A | 10 | 0 |
| Gasoline | Silver strips | B | 20 | 0 |
| Gasoline | Silver strips | K | 2 | 4 |
| Gasoline | Silver strips | K | 4 | 1 |
| Gasoline | Silver strips | K | 6 | 0 |
| Gasoline | Silver strips | K | 8 | 0 |
| Gasoline | Silver strips | K | 10 | 1 |
| Gasoline | Silver strips | K | 10 | 0 |
| Gasoline | Silver strips | K | 10 | 0 |

TABLE 10

Performance of Product L in Comparison to the Incumbent, Product A.

| Fluid | Metal | Product | Dosage (ppm) | Results |
|---|---|---|---|---|
| Gasoline | Silver wool | Blank | — | 2 |
| Gasoline | Silver wool | A | 2 | 0 |
| Gasoline | Silver wool | L | 2 | 2 |
| Gasoline | Silver wool | L | 3 | 0 |

TABLE 11

Performance of Product K in Copper Corrosion

| Fluid | Metal | Product | Dosage (ppm) | Results |
|---|---|---|---|---|
| Diesel | Copper | Blank | — | 2 |
| Diesel | Copper | K | 2 | 1 |
| Diesel | Copper | K | 5 | 1 |

TABLE 12

Effect of Sulfur Concentration on Copper Corrosion

| Fluid | Metal | Sulfur (ppm) | Results |
|---|---|---|---|
| Diesel | Copper | Blank | 1 |
| Diesel | Copper | 200 | 4 |
| Diesel | Copper | 100 | 4 |
| Diesel | Copper | 50 | 4 |
| Diesel | Copper | 20 | 2 |

When introducing elements of the present invention or the preferred embodiments(s) thereof, the articles "a", "an", "the" and "said" are intended to mean that there are one or more of the elements. The terms "comprising", "including"

and "having" are intended to be inclusive and mean that there can be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A method for preventing metal corrosion, the method comprising contacting an effective amount of an anticorrosion composition with a hydrocarbon-containing liquid, the hydrocarbon-containing liquid being in contact with a metal, the anticorrosion composition comprising a solvent and a compound of Formulae I or II:

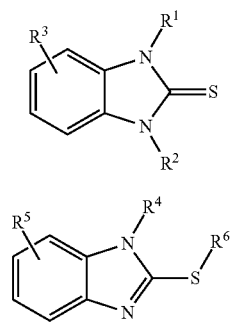

wherein
- $R^1$ and $R^2$ are independently substituted alkyl or unsubstituted alkyl;
- $R^3$ is hydrogen, substituted alkyl, or unsubstituted alkyl;
- $R^4$ is substituted alkyl, unsubstituted alkyl, substituted aryl, or unsubstituted aryl;
- $R^5$ is hydrogen, substituted alkyl, or unsubstituted alkyl; and
- $R^6$ is hydrogen, substituted alkyl, unsubstituted alkyl, or —S-heterocyclo.

2. The method of claim 1, wherein $R^5$ is other than hydrogen.

3. The method of claim 1, wherein the metal is silver, copper, or a combination thereof.

4. The method of claim 1, wherein $R^1$, $R^2$, and $R^4$ are independently substituted alkyl wherein one or more of the —$CH_2$— groups is replaced with a —C(O)—, or —O—, or one or more of the carbon atoms of the alkyl group is substituted with an amine group.

5. The method of claim 4, wherein $R^1$, $R^2$, and $R^4$ are independently —$(CHR^{22})_n$—$NR^{20}R^{21}$, wherein n is an integer from 1 to 4, $R^{20}$ and $R^{21}$ are independently alkyl, and $R^{22}$ is hydrogen or hydroxy.

6. The method of claim 5, wherein $R^{20}$ and $R^{21}$ are independently butyl, pentyl, hexyl, heptyl, octyl, isopropyl, 2-ethyl hexyl, sec-butyl, or sec-pentyl.

7. The method of claim 1, wherein $R^3$ and $R^5$ are independently hydrogen or unsubstituted $C_1$ to $C_6$ alkyl.

8. The method of claim 1, wherein the compound of Formulae I or II is selected from the group consisting of:

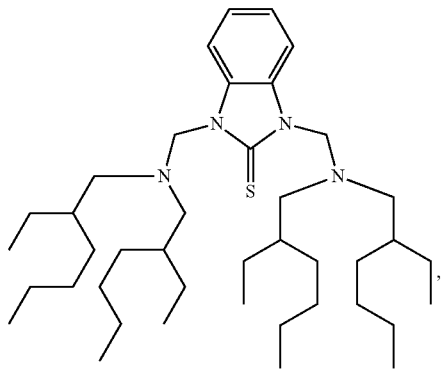

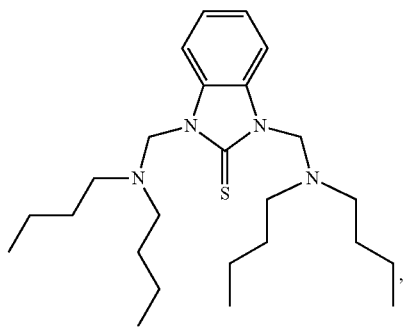

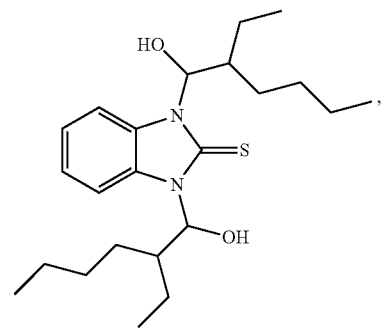

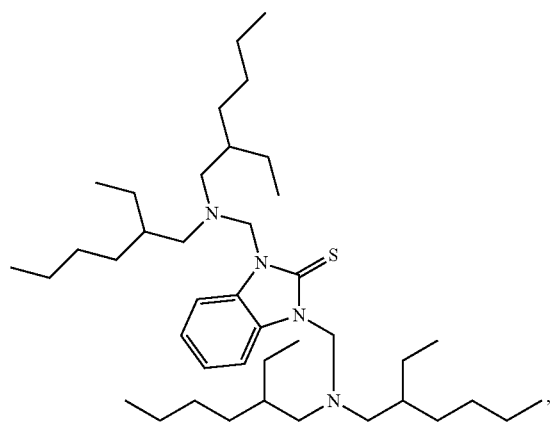

-continued

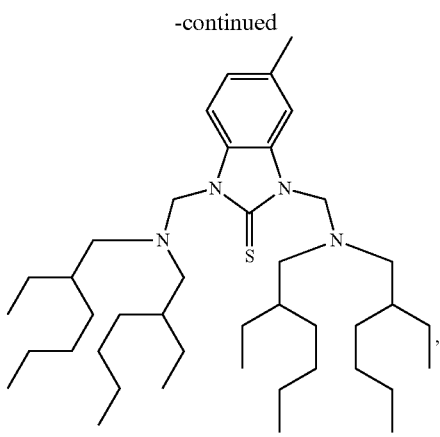

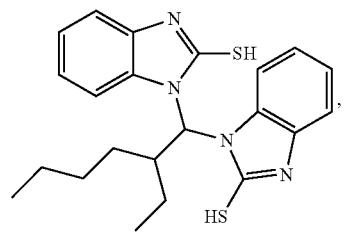

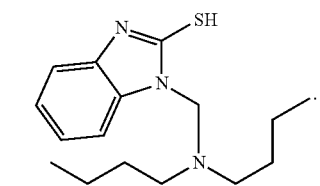

9. The method of claim 1, wherein the solvent comprises an aromatic solvent, an aliphatic solvent, a nitrogen-containing solvent, a glycol solvent, or a combination thereof.

10. The method of claim 9, wherein the aromatic solvent comprises heavy aromatic naphtha, toluene, kerosene, diesel, gasoline, reformate, or a combination thereof; the aliphatic solvent comprises hexane, heptane, octane, or a combination thereof; the nitrogen-containing solvent comprises N,N-dimethylformamide, 2-ethylhexylamine, or a combination thereof; and the glycol solvent comprises triglyme, diglyme, hexylene glycol, or a combination thereof.

11. The method of claim 1, wherein the anticorrosion composition further comprises a compound of Formulae III or IV:

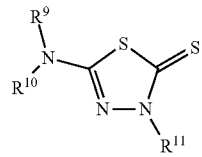

III

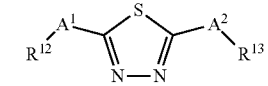

IV wherein $R^9$ and $R^{19}$ are independently hydrogen, substituted alkyl, unsubstituted alkyl, or together form an alkyliminyl;

$R^{11}$ is independently substituted alkyl, unsubstituted alkyl, substituted alkenyl, or unsubstitued alkenyl;

$R^{12}$ and $R^{13}$ are independently hydrogen, substituted alkyl, unsubstituted alkyl, substituted alkenyl, or unsubstitued alkenyl;

$A^1$ and $A^2$ are independently —S—, —N=C—, or —NR$^{14}$;

$R^{14}$ is hydrogen or substituted alkyl, or unsubstituted alkyl.

12. The method of claim 11, wherein $R^{11}$ is

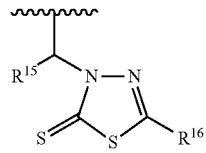

wherein $R^{15}$ is substituted or unsubstituted alkyl, $R^{16}$ is —N=CR$^{17}$, or NR$^{18}$R$^{19}$, $R^{17}$, $R^{18}$, and $R^{19}$ are independently hydrogen or substituted or unsubstituted alkyl, and the wavy line indicates the attachment of the substituent to the nitrogen of the ring.

13. The method of claim 11, wherein the compound of Formulae III or IV is selected from the group consisting of:

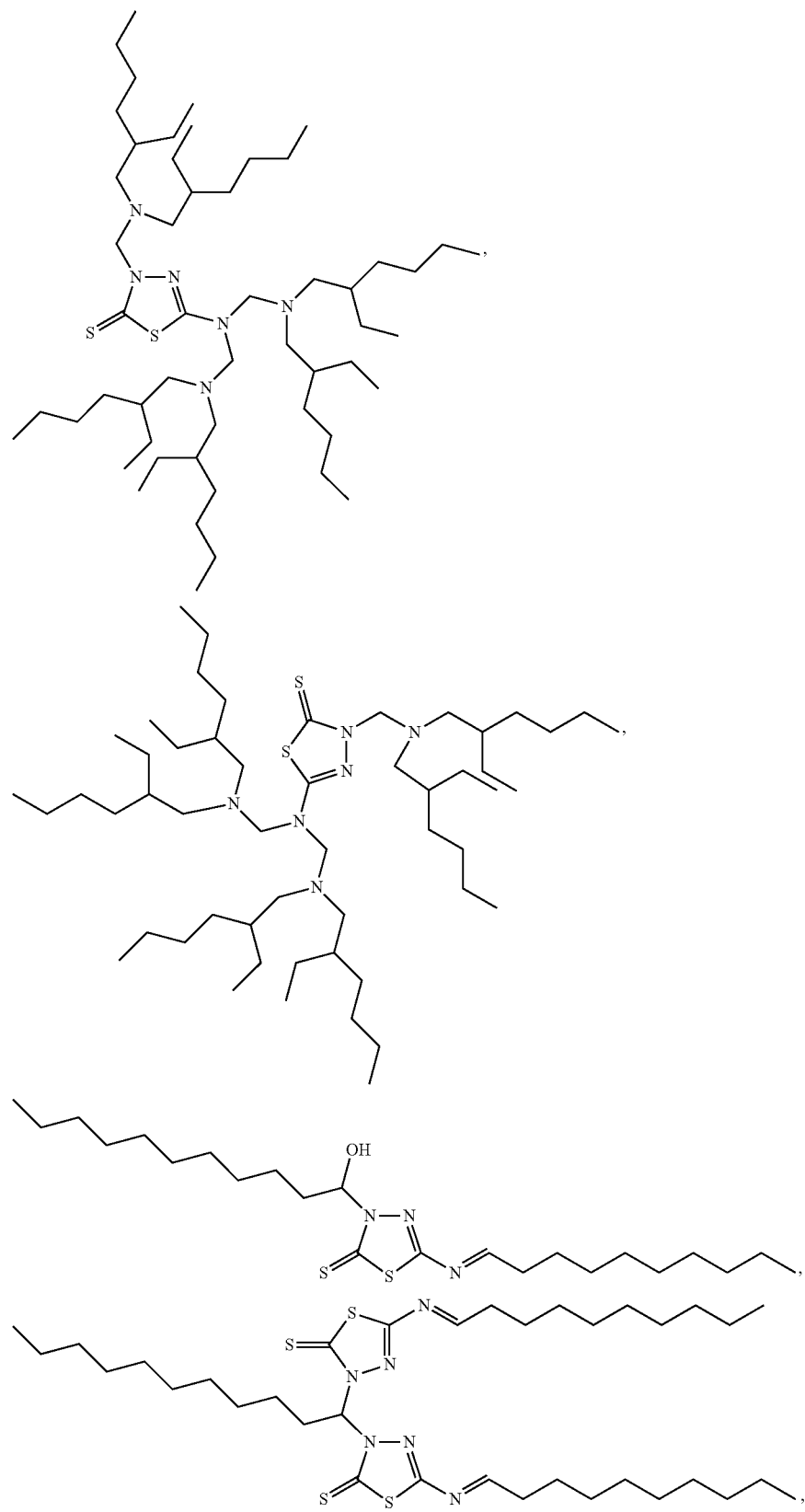

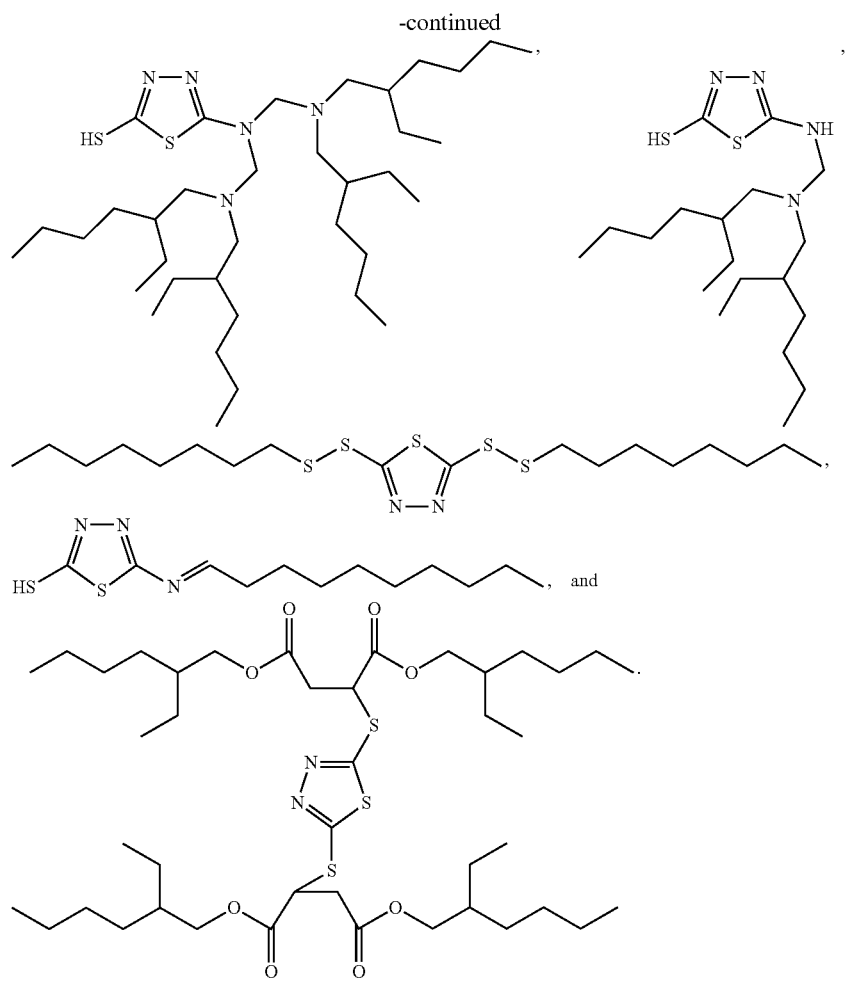

14. The method of claim 11, wherein a compound of Formulae I or II and a compound of Formulae III or IV are present in the anticorrosion composition at a concentration of from 5 to 30 wt. %, and 30 to 5 wt. % respectively, based on the total weight of the formulation.

15. The method of claim 11, wherein the anticorrosion composition is contacted to the hydrocarbon-containing liquid at a concentration from about 1 ppm to about 100 ppm.

16. The method of claim 1, wherein the hydrocarbon-containing liquid comprises gasoline, diesel, naphtha, jet fuel, kerosene, or a combination thereof.

17. A method for preventing metal corrosion, the method comprising contacting an effective amount of an anticorrosion composition with a hydrocarbon-containing liquid, the hydrocarbon-containing liquid being in contact with a metal, the anticorrosion composition comprising a solvent and a compound of Formula IIA:

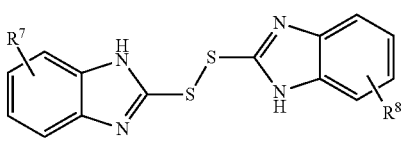

wherein $R^7$ and $R^8$ are independently hydrogen or alkyl.

18. The method of claim 17, wherein $R^7$ and $R^8$ are independently hydrogen or unsubstituted $C_1$ to $C_6$ alkyl.

19. The method of claim 17, wherein $R^7$ and $R^8$ are hydrogen.

* * * * *

UNITED STATES PATENT AND TRADEMARK OFFICE
CERTIFICATE OF CORRECTION

PATENT NO. : 10,457,817 B2
APPLICATION NO. : 15/584489
DATED : October 29, 2019
INVENTOR(S) : Kekeli Ekoue-Kovi et al.

It is certified that error appears in the above-identified patent and that said Letters Patent is hereby corrected as shown below:

On the Title Page

On Column 1, under Item (72) "Inventors":
"Hindalaga (IN)" should read "Hindalga (IN)"

On Column 2, under Item (56) "Other Publications", Line 5:
"olecular" should read "molecular"

In the Claims

On Column 39, Claim 7, Line 64:
"method of 1," should read "method of claim 1,"

On Column 42, Claim 11, Line 38:
Delete "unsubstitued" and insert -- unsubstituted --

On Column 42, Claim 11, Line 41:
Delete "unsubstitued" and insert -- unsubstituted --

On Column 42, Claim 12, Line 60:
Delete "NR18R19" and insert -- -NR18R19 --

Signed and Sealed this
Fourteenth Day of February, 2023

Katherine Kelly Vidal
*Director of the United States Patent and Trademark Office*